US012797118B2

(12) United States Patent
Soden et al.

(10) Patent No.: US 12,797,118 B2
(45) Date of Patent: Nov. 17, 2026

(54) ELECTROPORATION DEVICE

(71) Applicant: MIRAI MEDICAL LTD, Oranmore (IE)

(72) Inventors: Declan Soden, Oranmore (IE); Colin Forde, Oranmore (IE); Sean Kinsella, Oranmore (IE); Jason McNamara, Oranmore (IE); Cian Kerrigan, Oranmore (IE); Conor Hill, Oranmore (IE); Brian Harkin, Oranmore (IE); Oisin McGleenan, Oranmore (IE)

(73) Assignee: MIRAI MEDICAL LTD, Oranmore (IE)

( * ) Notice: Subject to any disclaimer, the term of this patent is extended or adjusted under 35 U.S.C. 154(b) by 163 days.

(21) Appl. No.: 18/840,092

(22) PCT Filed: Feb. 27, 2023

(86) PCT No.: PCT/EP2023/054883
§ 371 (c)(1),
(2) Date: Aug. 21, 2024

(87) PCT Pub. No.: WO2023/161492
PCT Pub. Date: Aug. 31, 2023

(65) Prior Publication Data

US 2025/0160920 A1 May 22, 2025

(30) Foreign Application Priority Data

Feb. 28, 2022 (EP) .................................... 22159282
Sep. 2, 2022 (EP) .................................... 22193694

(51) Int. Cl.
*A61B 18/00* (2006.01)
*A61B 1/018* (2006.01)

(52) U.S. Cl.
CPC .............. *A61B 18/00* (2013.01); *A61B 1/018* (2013.01); *A61B 2018/00077* (2013.01);
(Continued)

(58) Field of Classification Search
CPC ..... A61B 1/018; A61B 18/00; A61B 18/1492; A61B 2018/00077; A61B 2018/0016;
(Continued)

(56) References Cited

U.S. PATENT DOCUMENTS 5,256,141 A * 10/1993 Gencheff .......... A61M 25/0032
604/501
2010/0030256 A1* 2/2010 Dubrul ............... A61B 10/0266
606/200

(Continued)

FOREIGN PATENT DOCUMENTS

WO 2022265921 A1 12/2022

OTHER PUBLICATIONS

International Search Report issued in PCT/EP2023/054883; mailed May 12, 2023.

*Primary Examiner* — Tigist S Demie
(74) *Attorney, Agent, or Firm* — Studebaker Brackett PLLC

(57) ABSTRACT

A pulsed field delivery device for delivery of electroporation treatment to cancerous and pre-cancerous regions of the gastrointestinal tract is described. It has a first expanding body coupled non-conductively to a second expanding body wherein the non-conductive coupling allows elements of the expanding bodies to sit on opposite sides of a tissue across which pulsed electric fields are applied. An elongate shaft has a proximal end which extends exterior of the patient so that a user can advance and withdraw the device when required. The device also comprises an elongate member or sheath which can be advanced over or retracted back off of
(Continued)

the distal end of the device providing protection during device movement. The electrodes are arranged to radially expand and to move closer together to pinch diseased tissue being treated.

22 Claims, 19 Drawing Sheets

(52) U.S. Cl.
CPC ............... *A61B 2018/00178* (2013.01); *A61B 2018/00184* (2013.01); *A61B 2018/00267* (2013.01); *A61B 2018/00285* (2013.01); *A61B 2018/00767* (2013.01); *A61B 2018/00982* (2013.01)

(58) Field of Classification Search
CPC A61B 2018/00178; A61B 2018/00184; A61B 2018/00214; A61B 2018/00261; A61B 2018/00267; A61B 2018/00273; A61B 2018/00285; A61B 2018/00404; A61B 2018/00482; A61B 2018/00488; A61B 2018/00494; A61B 2018/005; A61B 2018/00517; A61B 2018/00535; A61B 2018/00613; A61B 2018/00744; A61B 2018/00767; A61B 2018/00982; A61B 2018/143; A61B 2018/1465; A61B 2018/1472; A61B 2018/1475; A61B 2218/002; A61B 2218/003
See application file for complete search history.

(56) References Cited

U.S. PATENT DOCUMENTS

| | | | |
|---|---|---|---|
| 2013/0204068 A1 | 8/2013 | Gnanashanmugam et al. | |
| 2014/0039491 A1 | 2/2014 | Bakos et al. | |
| 2015/0182282 A1* | 7/2015 | Zemel ................ | A61B 18/1206 606/41 |
| 2018/0296264 A1 | 10/2018 | DeSimone et al. | |
| 2019/0231425 A1* | 8/2019 | Waldstreicher .... | A61B 18/1492 |
| 2020/0398050 A1 | 12/2020 | Viswanathan et al. | |

* cited by examiner

ELECTROPORATION DEVICE

INTRODUCTION

The invention is in the field of electroporation.

An objective of this invention is to achieve improved access and delivery of electroporation treatment to the body, primarily but not exclusively in the lumen. An example is treatment of tumour tissue with electroporation in the gastrointestinal lumen.

Existing devices for delivery of electroporation intraluminally suffer from an inability to fully access the lumen due to tumour obstruction wherein visibility, access and transit on an endoscope is impeded.

Intraluminal tumours can extend several centimetres in length and cover the full circumference of the lumen. Disease progression and application of existing treatment modalities can induce injury to the surrounding tissue causing scarring and stenosis of the lumen. This reduces the function of the lumen and greatly limits access endoscopically. Full dilation of malignant tissue in a lumen presents a high risk of perforation or tearing, resulting in emergency surgery with an associated high rate of mortality Electroporation has become established as a safe and effective clinical tool which permeabilises the cell membrane and can enable the rapid passive diffusion and targeted uptake of therapeutic agents. However, application of an electrical field within a lumen is very challenging.

The application and positioning of two or more electrodes presents challenges within the lumen where access is limited and positioning of needle electrode(s) is impractical and if achievable may not ensure full coverage of the desired treatment area.

Existing alternative therapies involving tissue ablation (for example Radio Frequency Ablation, Microwave Ablation, Cryo Ablation) are associated with damage to the tissue structures including blood vessels and nerves and are associated with the risk of creation of unintended fistula. Thus, where these therapies are used, they are often used sparingly in their application in order to avoid inadvertent injury which in the case of cancer or pre-cancerous tissues treatment is in conflict with the physician's desire to remove or ablate all of the abhorrent tissue to prevent recurrence.

Electroporation leaves existing extracellular matrix and tissue structures intact and thus does not have these associated risks however its uptake thus far had been limited by the tools available for its delivery and targeting as up until now it has been most effectively applied where electrodes can be placed on two sides of the intended treatment zone.

The invention addresses these problems.

SUMMARY

The invention provides an electroporation probe as set out in any of probe claims appended hereto, and an electroporation device as set out in any of device claims appended hereto, and a method of electroporation treatment according to any of the method claims appended hereto.

We describe an electroporation probe comprising an elongate support, the support comprising electrical conductors and being configured to extend through a lumen of a human or animal body extending in a longitudinal direction with a longitudinal axis from a proximal end to a distal end, the support supporting at least two electroporation electrodes connected to the conductors and being mounted to engage tissue in the wall of a lumen in use, and an electrode actuator.

In some examples, at least one electrode is deformable for radial expansion from a retracted position. In some examples, the probe comprises a plurality of electrodes spaced apart in the longitudinal direction, and said radial expansion causes surfaces of a pair of electrodes to move closer together in the longitudinal direction with radial expansion, thereby contributing to gripping of tissue which protrudes internally into a lumen.

In some examples, at least one electrode has an operative configuration with a central radial peak in a central region and being sloped on each longitudinal side of the central region.

In some examples, the probe comprises a spacer between juxtaposed electrodes, and said spacer prevents movement of each electrode closer to the other electrode at the longitudinal axis, and the proximal end of a proximal electrode and the distal end of a distal electrode (4) are each coupled to the actuator to cause said ends to move toward each other to compress the electrodes against the spacer.

In some examples, at least one of the electrodes has a shape memory and is configured for at least some of said radial expansion upon removal of a constraint.

In some examples, the actuator is configured to cause axial compression of at least one electrode to force at least some of said radial expansion. In some examples, the electrode has a preferred expanded shape memory state to guide initial radial expansion and the actuator is configured to cause further radial expansion.

In some examples, the actuator is configured to allow a user to sense a level of force required by the actuator to cause radial expansion, thereby providing a user indication of when tissue is engaged and to what extent the tissue is being pushed by said further radial expansion.

At least one electrode is configured for radial expansion to exert a radial force to dilate soft, compliant tissue yet conform to harder stenosed tissue without causing dissection or perforation, said force being in the range of 0.1 $N/mm^2$ to 1 $N/mm^2$.

In some examples, the electrode or an expandable body to which an electrode is mounted is formed from a laser cut tube, which has been heat set to a preferential expanded shape to which it will return at or below body temperature if unconstrained. At least one electrode comprises a mesh with a 1-over-1-under-1 strand braiding pattern of strands having diameters in the range of 0.02 mm to 0.25 mm diameter. In some examples, said electrode comprises a number of strands in the range of 8 to 96.

In some examples, at least one electrode comprises a mesh comprising a structural layer of 8 to 24 wires having a diameter in the range of 0.15 mm to 0.35 mm, and a fine layer of 24 to 96 wires of diameter in the range of 0.01 mm to 0.1 mm. In some examples, the length in the longitudinal direction of at least one electrode is in the range of 0.5 mm to 75 mm.

In some examples, the longitudinal distance between at least two electrodes is in the range of 1 mm to 40 mm, optionally 2 mm to 20 mm.

In some examples, the probe comprises at least two electrodes of different stiffness, configured for different levels of penetration into tissue.

In some examples, at least one electrode is mounted to, or itself forms, an expandible mesh with:

- metal wire having diameters in the range of 0.1 mm to 0.35 mm, or provision of stiffness to the mesh, and
- metal wire having diameters in the range of 0.01 mm to 0.1 mm, for mesh flexibility.

In some examples:

the probe is for treatment of the GI tract and a maximum diameter after radial expansion is in the range of 30 mmm to 60 mm, or the probe is for treatment of the urethra and a maximum diameter after radial expansion is in the range of 10 mm to 15 mm, or, the probe is for treatment of the bile duct and a maximum diameter after radial expansion is in the range of 4 mm to 10 mm.

In some examples, at least one electrode is mounted to an expandable body for movement between said retracted and operative positions.

In some examples, the expandable body comprises an expandable mesh. In some examples, the expandable body comprises a mesh comprising at least two elements of different diameter and/or strength.

In some examples, the expandable body comprises a balloon to which an electrode is mounted.

In some examples, at least one electrode comprises a feature for extending radially into tissue in use. In some examples, the feature comprises a barb or a needle, and a laser cut tube has a barb feature as part of its laser cut pattern, optionally, one or more needle(s) may be shrouded. In some examples, at least one needle is shrouded.

In some examples, the probe comprises a physical separator between axially juxtaposed electrodes. In some examples, the probe comprises at least four axially separated electrodes and there is a separator between each successive electrode and the next electrode. In some examples, the probe comprises proximal and distal barrier balloons defining a space, in use, enclosing at least two expanding bodies, the space being to enclose aa fluid agent introduced into the space to assist electroporation.

In some examples, the probe further comprises an internal balloon to adjust volume of said space by being expanded to a desired extent.

In some examples, the internal balloon is located to act as an insulating spacer between juxtaposed balloons. In some examples, the probe comprises a spacer between axially spaced apart electrodes, and said spacer comprises a plurality of parallel spacer elements.

In some examples, at least one electrode has an operative position which is further from the longitudinal axis that the operative position of another electrode, and said electrodes are overlapped in the longitudinal axis but not contacting each other.

We also describe an electroporation device comprising a probe as described in any embodiment and an electrical drive for delivering pulses to the electrodes via the conductors.

In some examples, the electrical drive is configured to independently apply variable voltages, preferably from a generator linked with the proximal end of the probe. In some examples, the electrical drive is configured to provide pulses matching, or specific to, the electrode position.

In some examples, the actuator is configured to move the electrodes to an intermediate position between said retracted and operative positions, and the electrical drive is configured to provide pulses matching the intermediate electrode position. In some examples, the drive allows selective activation of specific electrodes.

In some examples, the device comprises an endoscope and wherein the probe has lateral dimensions in the retracted position to allow entry to the body via an endoscope instrument channel.

In some examples, at least some electrodes are movable axially, and the actuator is configured to move at least one electrode to optimise electrode spacing.

In some examples, the probe comprises a strain gauge or pressure sensor for providing feedback during electrode actuation, the sensor being configured to provide feedback on the force required to displace diseased tissue.

In some examples, the probe comprises a balloon expandable body to which at least one electrode is mounted and the actuator comprises a handle adapted to allow a user to feel the force required to inflate the balloon.

In some examples, the actuator comprises a mechanism and a user handle which is movable with a force related to the resistance to radial expansion of the electrode.

In some examples, the probe comprises a safety device to prevent application of force above a limit by an actuator. In some examples, the probe comprises a sensor for sensing patient tissue and/or for sensing the electrode position, and the actuator is configured to move the electrodes to a position in contact with tissue but not exerting forces in excess of 1 $N/mm^2$ on the tissue, to reduce chance of tissue dissection, and optionally said sensor comprises a strain gauge.

In some examples, the probe comprises a sensor to provide electrical feedback to system such as an electrical drive of the electrodes or expanding body.

In some examples, the probe comprises a conduit extending distally for delivery of a fluid at or near the electrodes. In some examples, the device comprises a fluid controller for controlling delivery of a fluid via said conduit. The controller may be configured to control fluid delivery according to position of the electrodes. The electrical drive may configured to control drive pulses according to delivery of a fluid, for example according to timing and electrical characteristics of the fluid. The fluid controller may be configured to cause delivery of any one or more of a foam and a liquid, and the fluid may include a therapeutic agent.

The electrical drive may configured to vary pulse voltages according to sensed parameters including one or more selected from: electrode position, conductivity of the region at the electrodes, and therapy timing regime. The fluid controller may be configured to cause administration of a foam directly to both tissue and surface area surrounding the device.

The foam may include a cationic solution such as lidocaine HCL with the aim of reducing the electrical field strength required for electropermeabilisation of the cell membrane.

We also describe a method of use of the device comprising inserting the probe along a lumen of a human or animal body until the electrodes are located at a longitudinal position of tissue to be treated, and actuating the electrodes to perform electroporation treatment of the tissue.

In some examples, the probe comprises a plurality of longitudinally spaced-apart electrodes, and the probe is positioned to provide an electric field in a region between two electrodes for treatment of tissue in said region. The electrodes may advantageously be moved radially to expanded positions at which they converge together to cause pinching of tissue in said region. Said tissue may be a pre-cancerous nodular polyp.

In some examples, the probe is moved to a series of a plurality of longitudinal positions and the electrodes are actuated at each said longitudinal position, and the positions are chosen so that there is a desired level of overlap in treated regions to achieve a desired level of electroporation in each region. The extent of overlap may be chosen to achieve RE or IRE.

A fluid may be injected into a region between two spaced-apart electrodes, to enhance electroporation in said region.

We also describe an electroporation probe having an elongate support with electrical conductors and extending from a proximal end to a distal end, the support supporting at least two electroporation electrodes connected to the conductors and being mounted to engage tissue in the wall of a lumen in use.

Preferably, the probe comprises an actuator to move the electrode in a direction having a radial component from a retracted or collapsed position to an operative position for contact with tissue. The probe may be part of a medical pulsed field delivery device for delivery of electroporation treatment to tissue in cancerous or pre-cancerous regions of a lumen such as the gastrointestinal tract. Preferably, the expanding body of the electrode is configured to engage with the tissue with sufficient force to ensure electrical contact between the electrode and the tissue is maintained during delivery of pulsed field electroporation.

Preferably, the expanding body of the electrode is configured to conform to tissue structures which are rigid and non-pliable, rather than forcing these to move or compress, thus ensuring a large contact area between electrode and the tissue while simultaneously ensuring the electrode does not cause perforation or dissection of the luminal tissue. When tissue structures are flexible/pliable, the electrode stretches the tissue to ensure adequate contact.

The probe may have a plurality of electrodes. An electrode may be movable by being mounted to, by being engaged by, or by being an integral part of, an expanding body. The expanding body may comprise a balloon.

Where there is a plurality of electrodes, they may be mounted to radially opposing sides, for contact with tissue across which pulsed electric fields are applied. Preferably, the electrodes are arranged to be collapsed during device delivery into the lumen. In one example, the actuator is configured to move the electrodes to an intermediate position between said retracted and operative positions. Preferably the probe has lateral dimensions to allow entry to the body via an endoscope instrument channel. The probe may comprise an expandible body supporting the electrodes.

The expandible body may comprise an expandible metallic wire mesh. Such a mesh may be of stainless-steel wire or of a shape memory alloy such as Nitinol. The expandible body may comprise a polymer mesh with attached or overlayed electrically conductive elements acting as the electrode. Preferably, the expandible body comprises materials that can deform during actuation without undergoing plastic deformation that impacts the ability of the device to be actuated from its collapsed to its expanded form repeatedly.

At least one expanding body may be formed from a laser cut tube such as a Nitinol tube, and preferably the tube has been heat-set to a preferential expanded shape to which it will return at or below body temperature if unconstrained. The tube may be held in its collapsed configuration by a user controlled elongate member until such time as the user allows its return to its preferred shape, and such a member may comprise a pull wire attached to one end of the heat set Nitinol which holds the collapsed the frame until such time as the user allows its return to its preferred shape.

In another embodiment the expanding body (such as a laser cut tube or wire mesh) has not been heat set to a preferred expanded state but rather can be actuated to such state as a result of the mechanical configuration of its body through positive action by the user. This might be achieved through movement of a pull or push wire or tubular member. In these situations, when Nitinol is used, it may be used primarily for its super-elastic properties which allow it to experience increased localised strain, like that seen during delivery through tortuous anatomy, without permanent deformation of its structure such that it will remain functional after delivery. In order to achieve this Nitinol's Active Austenite Finish Temperature (AAFT) must be suitably tuned such that the material operates within its super-elastic temperature window at the temperature at which the device is used in its operating environment.

In yet another embodiment the movement from collapsed to expanded state for the expanding bodies is some combination of heat set shape and mechanical configuration of the body. Preferably the actuator comprises a sheath which constrains the heat set tube until such time as the user allows its return to its preferred shape, to allow its expansion to the operative position.

The Nitinol mesh may have a pre-programmed (memory) expanded form to guide the shape and position of the expandable body (a) at initial delivery and (b) as the body is further expanded. This programming of the expandable body as it is expanding will help maintain optimum electrode gap, thereby optimum electrical field and also optimum tissue engagement. In yet another embodiment the pre-programmed expanded form may have a shape which ensures inter electrode distance is well maintained regardless of diameter at which device is deployed.

In some examples, the probe comprises a plurality of sets of electrodes spaced apart in the longitudinal direction. At least some electrodes may be moveable in relation to the next electrode to optimise electrode spacing and ensure adequate tissue contact.

In some examples there are a plurality of electrodes and at least one electrode has an operative position which is further from the longitudinal axis that the operative position of another electrode. In one example said electrodes are overlapped in the longitudinal axis but not contacting each other.

Preferably, the electrodes and/or the expanding body are configured to cause tissue being treated to be pulled in between electrodes during their expansion to their operative positions. In one example, the electrodes and/or the expanding body are configured to cause tissue to be pinched between the electrodes.

In one example an expanding body comprises a balloon and the electrodes are embedded in or on the balloon surface. In one example at least one electrode and/or an expanding body comprises a feature for extending into tissue in use, the feature comprising for example a barb or a needle. In one example a laser cut tube has a barb feature as part of its laser cut pattern. One or more needles may be partially or fully shrouded.

Preferably, the probe comprising a sensor for providing feedback during electrode actuation. In one example the sensor is configured to provide feedback on the force required to displace diseased tissue. The probe may be configured to provide user haptic feedback such that a user can feel an increase in force required to actuate the electrode from its collapsed to its expanded form as it displaces diseased tissue.

In one example, the expandible body comprises a balloon and the actuator comprises a handle adapted to allow a user to feel the force required to inflate the balloon. In one example, the actuator comprises a mechanism and a user handle which is movable with a force related to the resistance, imparted by the tissues to be treated, to expansion of the expandible body.

In one example, the mechanism has low friction between moving members such that when actuated from collapsed to expanded form while the body is unconstrained the force required is consistently low. In one example, the actuator is configured to limit mechanical advantage so that a user can perceive a ramp-up in force needed to cause expansion of the expandible body.

In one example the probe may be constructed such that the user can feel the increase in force required to actuate the electrode from its collapsed to its expanded form as it displaces diseased tissue. In practice achieving this through design depends on the choice of user actuated handle, for example if this is applied to the balloon driven expansion and a syringe style handle is used the user will feel the force required to inflate the balloons provided the lumen through which the inflation media is sufficiently rigid and does not itself introduce "noise". Achieving this with mechanical actuation, similarly, requires that the designer used suitably rigid materials for conveying actuation forces and desirably achieve low friction between all moving members such that when actuated from collapsed to expanded form while the device is in free air the force required is consistently low. It is also desirable to limit the amount of mechanical advantage given to the user during design of the actuation handle as this will correspondingly decrease their ability to perceive a ramp up in force that they need to apply in order to expand the expanding bodies.

In one example the probe may be constructed such that the user can feel the force required to actuate the electrode or electrodes from their collapsed to a partially expanded form such that the user determines that the electrodes are expanded sufficiently against tissue such as to create a reliable contact area with said tissue for delivery of electrical pulses with the understanding that additional expansion may result in undesirable effects on the lumen such as dissection or perforation. This may facilitate the end user in achieving successful safe treatment of areas which cannot be directly visualised, via the visual guidance of an endoscope's camera, or indirectly visualised using, using x-ray guidance. If end-users feel sufficiently comfortable with this mode of treatment this will allow treatment in a greater range of treatment settings including ambulatory healthcare settings.

In one example the probe may be constructed such that the electrodes actuation is mechanically or pneumatically connected such that during electrode actuation electrodes expand to different diameters depending on the lumen diameter and tissue stiffness surrounding the individual electrodes, in this way the user senses during performance of the action to actuate compound force feedback from the group of electrodes.

In one example the probe comprises a safety device to prevent application of force above a limit by the actuator, and the limit may be user defined. In one example the probe comprises a channel extending distally for delivery of a fluid, preferably at or near the electrode.

In one example, the probe comprises a sensor to provide electrical feedback to system such as an electrical drive of the electrodes or expanding body. In one example, the prove comprises a sensor for sensing patient tissue and/or for sending the electrode position, and the actuator is configured to move the electrodes to a position in contact with tissue but not exerting forces on the tissue, to reduce chance of tissue dissection.

We also describe an electroporation device comprising a probe of any example described herein, and an electrical drive for delivering pulses to the electrodes via the elongate support conductor. The electrical drive may be configured to independently apply variable voltages, preferably from a generator linked with the proximal end of the probe.

In one example, the electrical drive is configured to provide pulses matching, or specific to, the electrode position. In one example, the actuator is configured to move the electrodes to an intermediate position between said retracted and operative positions, and the electrical drive is configured to provide pulses matching the intermediate electrode position.

The actuator may be user-operable, or in other examples it is automatic. The drive may allow selective activation of specific electrodes. The device may comprise a conduit for delivery of a fluid via the elongate support. The device may comprise a fluid controller for controlling delivery of a fluid via said conduit. The controller may be configured to control fluid delivery according to position of the electrodes. Preferably, the electrical drive is configured to control drive pulses according to delivery of a fluid, for example according to timing and electrical characteristics of the fluid.

The fluid controller may be configured to cause delivery of any one or more of a foam and a liquid. The fluid may include a therapeutic agent.

Preferably, the electrical drive is configured to vary pulse voltages according to sensed parameters including one or more selected from: electrode position, conductivity of the region at the electrodes, and therapy timing regime.

In various examples, the expanding body is configured to engage with tissue with sufficient force to ensure electrical contact between the electrode and the tissue is maintained during delivery of pulsed field electroporation.

In various examples, the expanding body is configured to conform to tissue structures which are rigid and non-pliable.

In various examples, the expanding body comprises materials that can deform during actuation without undergoing plastic deformation.

In various examples, the expanding body comprises a mesh having a shape memory expanded form to guide the shape and position of the expanding body at initial delivery and as the body is further expanded, to maintain an optimum electrode gap.

In various examples, the expanded form has a shape which ensures inter-electrode distance is well maintained regardless of diameter at which device is deployed.

In various examples, the probe comprises a plurality of sets of electrodes spaced apart in the longitudinal direction, and at least some electrodes are moveable in relation to a next electrode to optimise electrode spacing and ensure adequate tissue contact.

In various examples, the probe is adapted to provide haptic feedback to allow a user to feel a force required to actuate the electrode or electrodes from their collapsed to a partially expanded form.

In various examples, the electrodes are mechanically or pneumatically connected to provide aid haptic feedback.

In various examples, the expanding body comprises a mesh network of a material such as nickel titanium alloy, Nitinol, strands interwoven to achieve a basket form which can be collapsed down by pulling the mesh ends in opposing direction using attached cuffs. In various examples, the mesh is constrained in a 1-over-1-under-1 pattern. In various examples, the expanding body comprises a 1-over-1-under-1 pattern braiding of strand diameters in the range of 0.02 mm to 0.25 mm diameter, preferably 0.1 mm to 0.2 mm diameter.

In various examples, the expanding body comprises wires of two or more different diameters or materials, one diameter or material which imparts the required strength to the body for actuation while the other diameter or material is more flexible and more tightly packed, imparting conforming characteristics to the expanding body and ensuring optimum tissue contact. In various examples, the expanding body is oversized for the intended treatment lumen by 20% to 800% diametrically, preferably 20% to 500%.

In various examples, the expanding body is oversized for the target vessel this contact area expands axially as the electrode is further actuated from collapsed to expanded state creating an annular cylindrical contact area which allows greater delivery of energy to the lumen and thus opportunity for larger electroporated volumes.

In various examples, the expanding body comprises strands of a material such as Nitinol, configured to undergo a heat set step in its production which imparts to it preferred electrode shapes which have desirable attributes.

In various examples, the probe further comprises a physical separator between axially juxtaposed expanding bodies. In various examples, the probe comprises at least four axially separated expanding bodies and there is a separator between each successive body and the next body.

In various examples, the probe comprises proximal and distal barrier balloons defining a space, in use, enclosing at least two expanding bodies, the space being to enclose aa fluid agent introduced into the space to assist electroporation. In various examples, the probe further comprises an internal balloon to adjust volume of said space by being expanded to a desired extent. In various examples, the internal balloon is located to act as an insulating spacer between juxtaposed balloons.

In various examples, the probe comprises at least two expanding bodies of different stiffness, configured for different levels of penetration into tissue. In various examples, the probe comprises at least two expanding bodies of different stiffness, configured for different levels of penetration into tissue, said differences being in response to per-body individual adjustment by an actuator.

In some examples, the expanding bodies are expanded by one user action but said expanding bodies control method is linked such that in expanding to contact tissue one or more expanding body may reach a greater expanded diameter than one or more other as a result of balancing of forces exerted by the tissue on the expanding bodies.

In some examples, the expanding body actuation can be independently controlled by the user allowing user control over individual electrode expanded diameter.

BRIEF DESCRIPTION OF THE DRAWINGS

The invention will be more clearly understood from the following description of some embodiments thereof, given by way of example only with reference to the accompanying drawings in which:

FIG. 1(*c*) is a pair of views showing movement of expanding elements and corresponding tissue capture.

DETAILED DESCRIPTION OF THE INVENTION

Figure 1A:
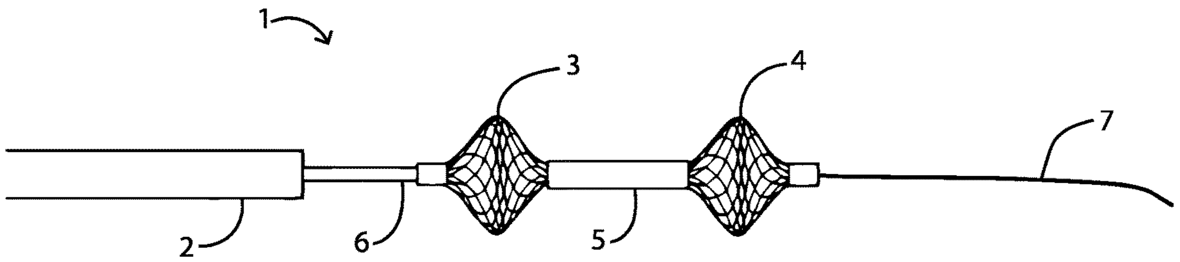
FIG. 1(*a*) is a side view of an electroporation probe of the invention in a partially expanded state with a delivery sheath retracted, FIG. 1(*b*) is a view of the device in a collapsed state.

Referring to FIGS. 1 to 4 there is illustrated an electroporation probe 1 of the invention for linking with an electroporation electrical drive. The probe 1 is for delivery of electroporation treatment to cancerous and pre-cancerous regions of the gastrointestinal tract. The probe 1 comprises a sheath 2 within which there is a shaft 6 and within which there is a delivery wire 7. Two electrical conducting wires, not shown, extend within the shaft 6 for linking an electrical drive to the sets of electrodes on expanding bodies 3 and 4 separated along the longitudinal axis by an isolating spacer 5. An electroporation device of the invention comprises the probe 1 and an electrical drive. The drive may for example be that described in our published specification WO2021/043779, the contents of which are incorporated herein by reference.

The drive may comprise a main controller linked with a user interface and with a probe drive circuit, the controller and the interface providing the user-side functions, whereas the drive circuit provides the pulses to probe electrodes.

The drive circuit comprises:

- a pulse control unit which is separated by opto-isolators from the remainder of the drive apparatus, to avoid high voltages being inadvertently transferred to the low-voltage control electronics,
- a high voltage generator with a transformer, providing up to 5 kV across capacitors,
- a pulse switching controller for delivering high frequency bi-polar pulses to an array of seven probe electrodes, and
- a voltage set and maintain circuit.

A touch screen interface is operably coupled to the drive controller which manages the generation of the high voltages and the pulse control, and the voltage, pulse duration, polarity and orientation. This level of control is achieved via the series of control circuits.

The controller is configured in some examples to apply to each electrode a ramp-up ($t_r$) duration of less than 0.5 μs to a plateau (U) amplitude in the range of 100V to 3000V for a duration in the range of 1 μs to 5 μs, and a ramp-down ($t_f$) duration from said voltage of less than 0.5 μs for each probe electrode terminal. The amplitude is in some examples in the range of 700V to 1600V and the pulse plateau duration is in the range of 1 μs to 3 μs, and preferably the energized on time during which pulses are delivered is in the range of 100 μs to 300 μs. Preferably, pulses are delivered in immediate succession. Preferably, the bipolar frequency is in the range of 100 kHz to 500 kHz.

The switch controller receives a low-voltage DC input of say 48 V. This input level sets the resultant pulse intensity level delivered to the probe 1. The switch controller adjusts the time that the transformer primary is energised to control the output voltage on the capacitors. Feedback from the output to the switch controller (with suitable isolation through medical grade optocoupler devices) enables the voltage to be precisely set and maintained. Thus, the capacitor output voltage can be varied over a large range (typically 100V to about 5 KV).

Figure 1B:
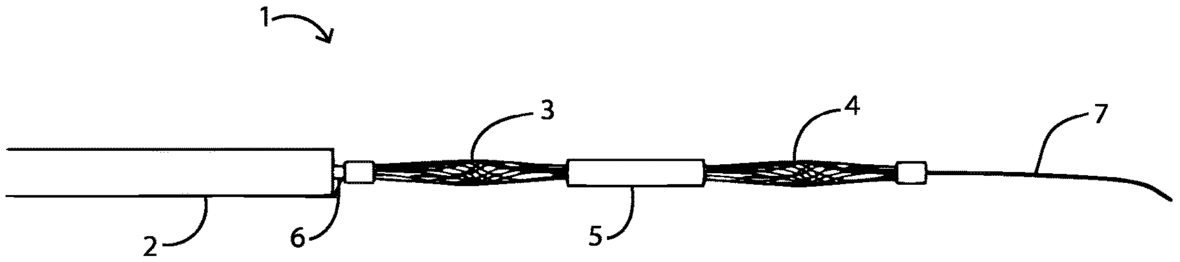
Figure 1C:
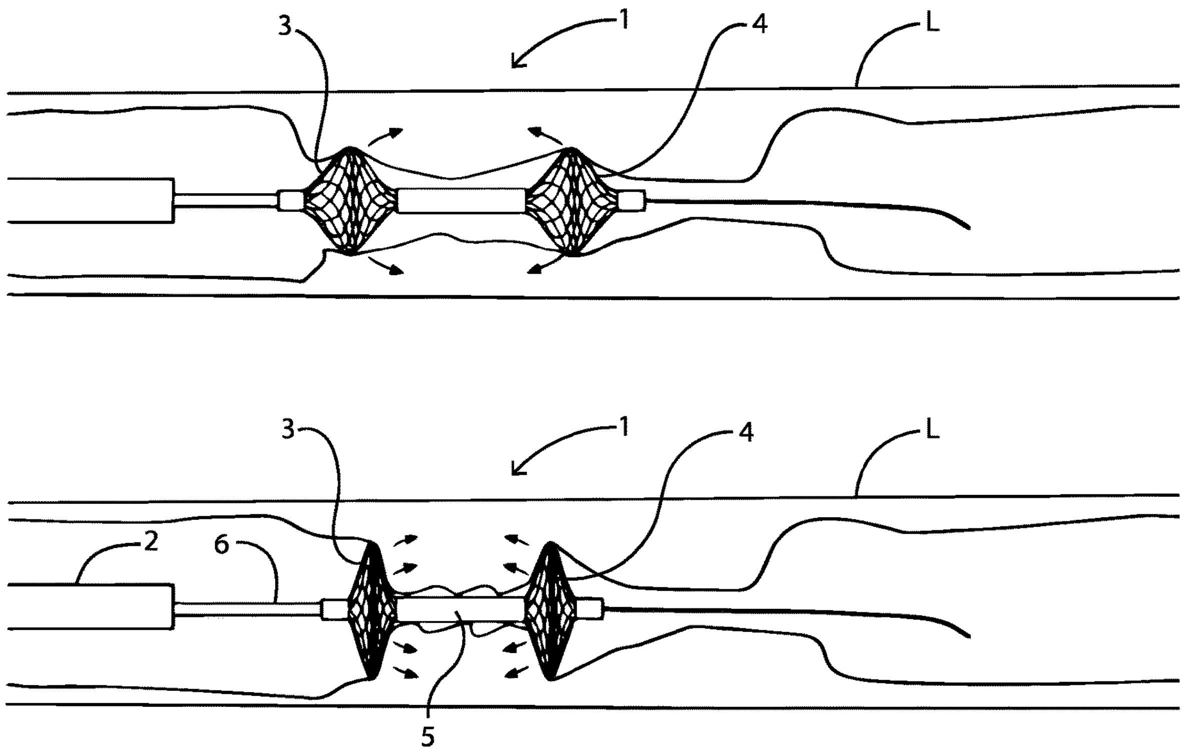

As shown in FIG. 1(*a*) each electrode 3 and 4 is an expanding body y having central radial peak in its central region, and a sloped regions on each longitudinal side of the central region. FIG. 1(*b*) shows them when collapsed, and FIG. 1(*c*) shows the bodies 3 and 4 when engaging tissue around a lumen, in this case the GI tract. As is clear from this diagram, the expanding bodies tend to pinch and engage with tissue so that there is tissue within a notional envelope or cylindrical region defined by the expanding body peaks. The top and bottom diagrams of FIG. 1(*c*) show different examples of this.

The probe can expand in an occluded vessel. Preferably, at least one electrode is in the form of, or is mounted to, an expanding body (or "expandable body", or "basket") which will dilate compliant tissue to ensure adequate contact and encourage surrounding tissue to fall between the expanding bodies. In other embodiments, the expanding body is constructed as to conform to tissue structures which are rigid and non-pliable, rather than forcing these to dilate, move or compress, thus ensuring a large contact area between electrode and the tissue while simultaneously ensuring the electrode does not cause perforation or dissection of the luminal tissue.

The basket may be manufactured with Nitinol, taking advantage of the shape memory capabilities for expansion when unsheathed. However, more secure expansion may be incorporated into a hand controller, probably as a slider or thumb wheel mechanism for actuation. The device may be required to expand to different diameters based on the lumen being treated and the shape of the lesion being treated, which depends on the pre-cancerous tissue geometry or the stage of cancer, which influence tumour geometry, stage of cancer developed in the patient from 4 mm-40 mm. Again, this may be in the form of expansion control by the clinician using the hand control or a family of devices, each a different size performing the same task in differently occluded vessels. In various examples, the expanding body comprises wire of two or more different materials, one or more materials which impart the overall mesh shape but are non-conductive and constrains another material or materials which somewhat contributes to the mesh form but primarily act as the electrodes through which electrical pulses are delivered.

The expanding body may be made up from any desired number of struts (for example members extending from the elongate support, then approximately parallel to the longitudinal axis, and then back into the elongate support), for example 6 to 192 struts, and the struts may be arranged circumferentially. The axial parts of the struts act as the electrodes to deliver the pulses. Within the scope of the electrode design, the addition of sensors wired to the electrodes is possible. These sensors may include but are not limited to impedance sensors, location/device proximity sensors and temperature sensors for example.

The sensor may comprise a strain gauge or pressure sensor for providing feedback during electrode actuation, the sensor being configured to provide feedback on the force required to displace diseased tissue.

The expanding body may be made up of a mesh network of nickel titanium alloy, and/or Nitinol, and preferably strands are interwoven to achieve a basket-like form which can be collapsed down by pulling the mesh ends in opposing direction using attached cuffs. This mesh may be the tightly constrained 1-over-1-under-1 pattern most common in braided tubes or a less constrained pattern which allows more strand freedom such as the 1-over-2-under-2 pattern further enhancing the ability of the mesh to conform to irregular tissue morphologies. The mesh expanding body utilizing 1-over-1-under-1 pattern braiding may be comprised of strand diameters in the range of 1 mm to 10 mm diameter, preferably 4 mm to 8 mm diameter. Nitinol strands resulting in the ideal combination of strength, elasticity, current carrying capacity and surface area for conforming to irregular tissue morphology and delivering pulsed field electroporation.

The expanding body may comprise two or more different wire diameters or materials, one diameter or material which imparts the required strength to the basket for actuation while the other diameter or material is more flexible and more tightly packed, imparting conforming characteristics to the expanding body and ensuring optimum tissue contact. Nitinol wire diameters in the range of 0.125 mm to 0.25 mm, preferably in the range of 0.15 mm to 0.20 mm are desirable for provision of stiffness to the mesh basket form while Nitinol wire diameters in the range of 0.025 mm to 0.1 mm, preferably in the range of 0.025 mm to 0.075 mm are desirable for creation of a flexible mesh with small openings in between the larger diameter strands. For example, a basket of eight 0.2 mm diameter nitinol wires and forty 0.05 mm diameter Nitinol wires will have the enhanced strength of including some 0.2 mm diameter wires with a corresponding smaller wrap diameter and smaller inter wire gaps in the basket as a result of the inclusion of 0.05 mm diameter wires in greater number than would be possible with larger wire diameters.

An additional benefit of the use of a stiffer wire for overall electrode shape in conjunction with less stiff wire is the ability of this overall construction to be fine-tuned to improve the ability of the electrode to grip tissue as the less stiff wire will somewhat deform away upon contact with the tissue during deployment while the stiffer wire will deform to a lesser extent creating a surface that interacts with the tissue that could be described as bumpy or rough akin to the addition of ridges to tires to improve grip.

The expanding body in going from its collapsed to its expanded state to contact the target vessel the device may undergo a large percentage diameter change, up to 1000%. In addition, it may be oversized for the intended treatment lumen by 20 to 800 percent diametrically, preferably 20 to 500 percent. This additional oversizing ensures that during actuation from a collapsed to an expanded stated the electrode body encounters tissue and is forced to conform to said tissue due to the expanding bodies inherent design and material composition. Having contacted tissue at one point all around the vessel the electrode has a narrow electrical contact area that is circular or elliptical, were the electrode not oversized this may be the contact area for delivery of pulses. When the expanding body is oversized for the target vessel this contact area expands axially as the electrode is further actuated from collapsed to expanded state creating a cylindrical contact area which allows greater delivery of energy to the lumen and thus opportunity for larger electroporated volumes. For this reason, a larger percentage oversizing will allow the user to, through movement of the actuator controlling deployment, decide on the effective length of each electrodes contact area.

The expanding body may include strands of a memory material such as Nitinol and undergo an additional heat set step in its production which imparts to it preferred electrode shapes which have desirable attributes, for example the expanding body ends may be bulbous in shape resulting in more consistent inter electrode distance at varying treatment diameters. This in turn will result in more consistent v/cm electric field strengths imparted to treated tissue.

The expanding body may incorporate an outer and an inner series of electrodes that will be oppositely charged to provide optimal electroporation to the tissue. The wires are delivered through the lumen and will not be exposed. The device may have capabilities to deliver foam to the lesion via small holes in the electrode struts, down the devices elongate body in a lumen for said delivery or through the overlayed sheath. This will likely be the case for pre-cancerous or early-stage oesophageal or colon cancer treatment whereby the electrode struts are coated in a foam allowing for delivery of higher electroporation voltages.

The device may be wired internally through a multi lumen extrusion with 2 to 20 lumens and a sheath on top to contain the body from expanding. The active length of the electrode is between 5 mm and 150 mm in length which is the length of the lesion that can be treated circumferentially by the pulses delivered.

Each expanding body/electrode may be movable in relation to the next electrode to optimise electrode spacing and ensure adequate tissue contact. In one embodiment this is achieved through having each electrode attached to a separate elongate member, each elongate member stacked inside the next with the ability to slide independently of each other. The user would control the sliding action via a hand controller.

An alternative embodiment of the device incorporates spring-loaded deployment and recapturing functionality.

The electrically connected expanding bodies of any embodiment may include Nitinol, or another self-expanding material, making use of the shape memory capabilities of the material to conform to their original set shape when deployed from a delivery catheter under control of the clinician via the hand controller. The expanding bodies ('baskets') may comprise any of a range of other materials which can be designed such that they can be actuated from a collapsed to an expanded state. Another embodiment uses a polymeric balloon to expand a flexible electrode fabric in order to create a similar electrode shape. It is estimated the length of each expanded basket, in its expanded shape, will be 0.5 mm to 75 mm but more preferably 1 mm to 5 mm with a diameter of 4 mm to 40 mm. The distance between the baskets is ideally 2-20 mm (but could range from 1 to 40 mm).

In some embodiments the entire expanding body, such as a mesh, acts as the electrode, and in other embodiments a portion of the mesh is constructed of non-conductive elements or shrouded to prevent its acting as an electrode. This may be used in manufacturing a device where a subset of the full 3600 is configured to perform electroporation. A method of achieving this involves producing the mesh from both conductive and non-conductive wire.

Sample Uses

To position the probe, in one example an endoscope is positioned upstream of the lesion and a guidewire is advanced through the narrowed Oesophagus before the sheathed device is advanced to the distal region of the malignant tissue.

Treatment may be performed with delivery of electroporation pulses alone or in combination with a therapeutic agent. Such agents include chemotherapeutic drugs, calcium or a foam solution.

The procedure is performed by placing the probe distal end at the distal end of the lesion, actuating/expanding the device and delivering the required pulse, then collapsing and retracting the device a known length before actuating again and pulsing to treat the next area. This can be repeated until the full tumour length is treated. The device in its initial positioning and deployment is essentially a bipolar electrode, with a capability of generating an electrical field in one place. When deployed, and preferably at least two electrodes expanded, the electrodes operate on multiple planes to generate a more homogenous electrical field.

In some cases, the length of the tumour will be greater than the distance between the electrodes (5-20 mm). During a procedure, for an occlusion of greater length than the gap between the electrode baskets, the pulses are delivered, and the device is collapsed before advancing further into the tumour (or if starting at the furthest point of the tumour, the device will be retracted rather than advanced). Once past the electroporated region, the device is redeployed, and pulses delivered. This process is repeated until the clinician is satisfied that they have covered the malignant tissue successfully. Some overlap of electroporated areas may be required to ensure full tumour treatment.

In another embodiment, the device may be configured such that clinically relevant irreversible electroporation is only achieved through two or more applications of the programmed pulse train to a given fragment of tissue. This may be advantageous for lesion lengths in excess of the length of the active portion of the device where an overlap region is required to prevent gaps between each pulse delivery and ensure adequate treatment. The clinician using the device can be trained to deliver a pulse, collapse, advance or retract the device by some portion of its active length, expand and deliver a subsequent pulse repeating this until the full lesion length has been covered with the overlap region which has undergone sufficient dosage being the treated region. This method of device configuration and use would lessen the potential for a clinician to miss portions of tissue as a result of inadvertent movement of the device by a distance in excess of the active length. This method of treatment would also decrease the impact of any single device placement being in some manner “sub-optimal”.

The actuator of the device may include a handle with a slider mechanism with multiple positions, allowing for expansion to a range of diameters from for example 2 to 30 mm depending on the presentation of the tumour. After being released from the sheath, a setting to lock the device in its expanded position and a collapsed setting to relax the basket allowing for the device to be pulled upstream to the next position. This part of the procedure varies with the drug delivery method, if present. The device may not need to be fully re-sheathed in some cases to be repositioned, the tension can be relaxed and the device pulled back through the lesion to the next treatment zone before the clinician re-deploys the device fully and locks the position.

In another embodiment, the device handle may include a slider mechanism for actuation of deployable needles from the device distal end. This may be achieved by movement of a push/pull elongate member which is attached to a sleeve. The sleeve may be manufactured from a laser cut tube from which the needles have been laser cut and remains part of or alternatively to a sleeve which the needles have been attached to by other means.

This force to cause actuation could equally be conveyed from user to the needle sleeve through pneumatic means.

In another embodiment, the parallel surfaces of a balloon, if present, may have attached a flexible electrode which would allow further electroporation to be delivered between the needles or in cases where use of the needles may pose excessive risk to the patient.

In another embodiment, a metal frame is used instead of a balloon to direct needles radially outward to contact the tissue. These may be deployed from the arms of a basket shape. The strut diameter is in one preferred example 0.6 mm (could be 0.3 to 1.9 mm in other examples). Heat set Nitinol may be used to deploy when unsheathed through a delivery sheath, ideally delivered through the biopsy channel of the endoscope but could also be delivered over a guide wire or a sheath attached to the outer surface or tip of the endoscope. The needles are deployed after the basket is expanded. Needles may be located in hollowed arms of the basket and deployed using a push pull mechanism which could be mechanical, electrical, magnetic, pneumatic or hydraulic.

A procedure may be performed endoscopically, using a live feed camera for guidance with either a single or double channel endoscope; this is dependent on the treatment method. For delivery of a fluid to enhance electroporation (for example IV Bleomycin and/or foam), a single channel endoscope is sufficient, while a double channel endoscope may be used for Calcium injection treatment method. An advantage of this device is that there is no visual obstruction or obscuring caused by the device blocking a camera lens. Hence, the clinician is more likely to achieve correct device placement for optimal performance.

In some examples, once the scope has been appropriately positioned in the distal region of the lesion, a guidewire is delivered through the working channel before the device is advanced. The guidewire is removed, and the device is unsheathed, expanding the electrode body, such as a Nitinol basket. The body is fully expanded, encouraging ingress of cancerous or pre-cancerous tissue before the electroporation pulses are delivered. At this point, the clinician may have the ability to increase/decrease the expanded diameter using a push/pull wire linked to the handheld controller. The device can then be re-sheathed and retracted along the lesion to the next treatment zone. This may be repeated until the full treatment zone has been electroporated successfully. For procedures involving foam or Calcium, additional steps are required.

The expanding bodies 3 and 4 of the probe 1 each comprises a mesh of strands which are all conductive.

The actuator has cables along the sheath 2 which allow the bodies 3 and 4 to be compressed to reduce the axial dimension but increase the radial dimension, as shown in FIGS. 3(*f*) and 3(*g*).

Figure 2:
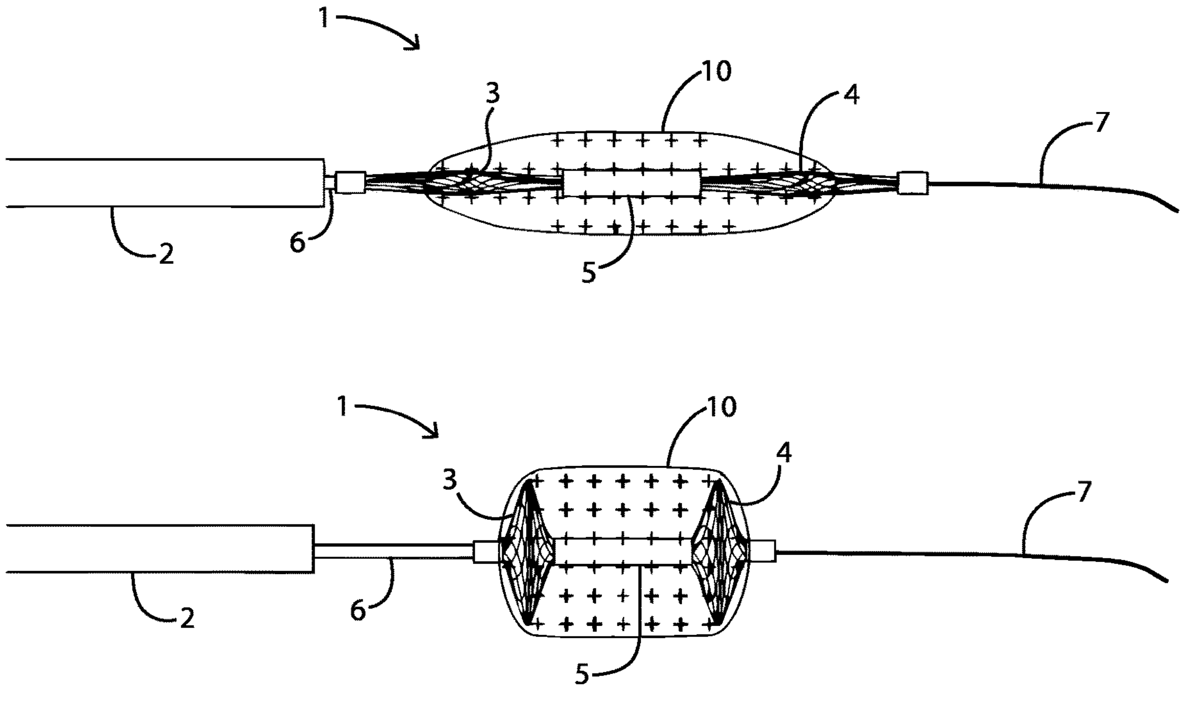
FIG. 2 is a pair of views illustrating how a notional area electroporated by an electric field changes if pulses are delivered in a fully collapsed state versus that of a fully expanded state, FIGS. 3(*a*) to 3(*g*) illustrate a full treatment of one portion of a lumen in seven stages from device introduction to pulsing, FIGS. 4(*a*) and 4(*b*) are side view diagrams illustrating the difference in electric field size as a result of the addition of barbs/tines to the expanding body, FIG. 4(*a*) without barbs and FIG. 4(*b*) with barbs, FIGS. 5(*a*), (*b*), and (*c*) are a set of three diagrams illustrating examples of electrically connected expanding bodies for electroporation probes of the invention: (a), wire mesh; (b) laser cut tube; (c) balloon with an electrically conductive overlay or embedding.
Figure 3A:
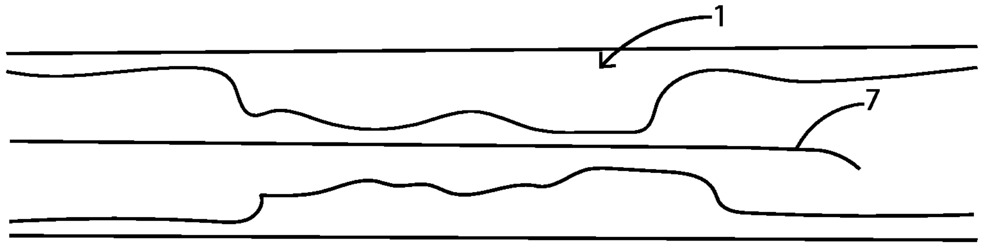
Figure 3B:
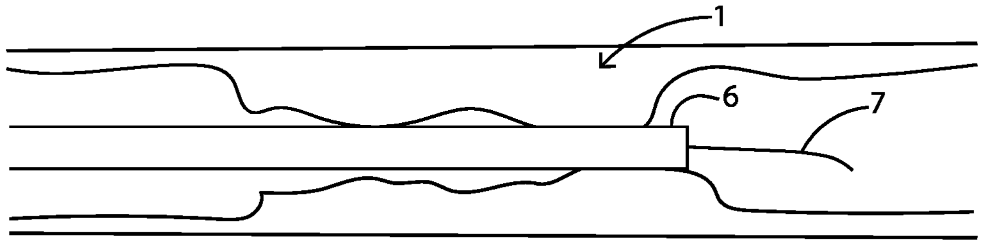
Figure 3C:
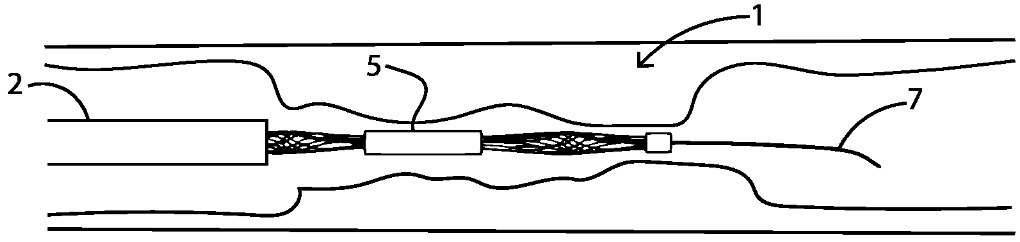
Figure 3D:
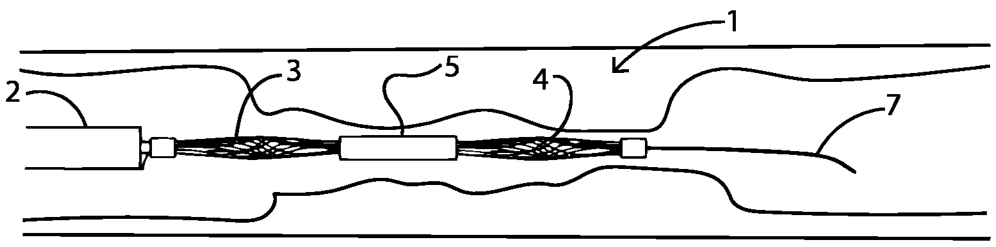
Figure 3E:
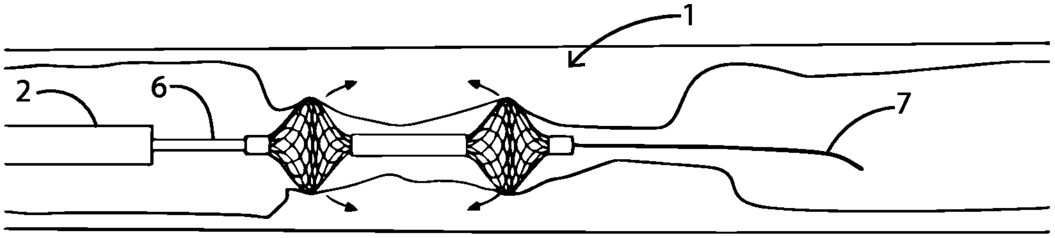
Figure 3F:
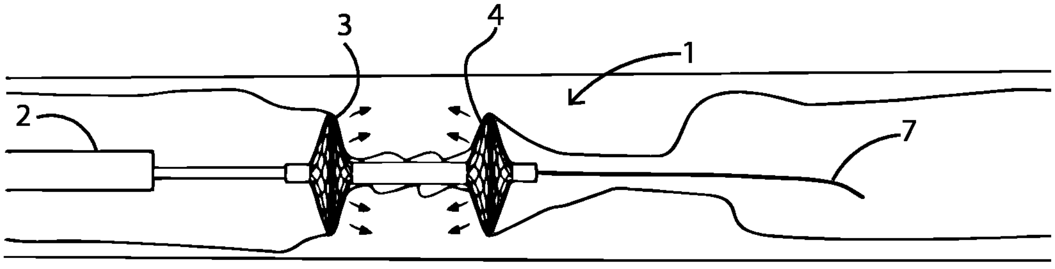
Figure 3G:
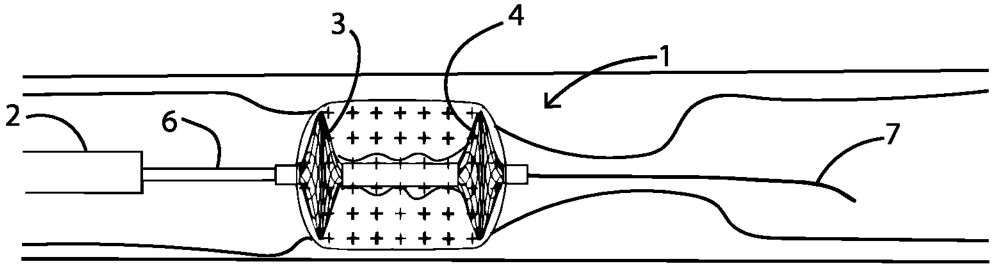

FIG. 2 shows use of the probe, with “+” symbols and a surrounding outline illustrating a notional envelope, indicated by the numeral 10, that encompasses the tissue expected to achieve successful electroporation through application of electrical pulses. When the bodies 3 and 4 are collapsed the envelope is narrow, but much wider when they are expanded.

FIGS. 3(*a*) to (*g*) show use of the probe 1 in a greater number of diagrams, in sequence from top down, (a) to (e):

(a) Pushing of the distal end of the probe, with the guide wire 7 entering the lumen region where the tissue is to be treated.

(b) The shaft 6 enters this region.

(c) and (d) The shaft (or sleeve) is retracted to expose the expanding bodies 3 and 4 in the lumen (L) where there is the greatest narrowing due to a lesion.

(e) to (g) This causes the expanding bodies 3 and 4 to expand, initially with a longer longitudinal dimension, and as the peaks enter the tissue the longitudinal dimension decreases and the volume between the bodies 3 and 4 increases. In an alternative arrangement the radial expansion can be fully or partly caused by axial compression by an actuator.

Figure 4:
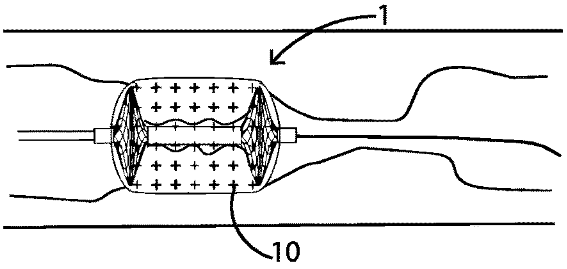
Figure 4:
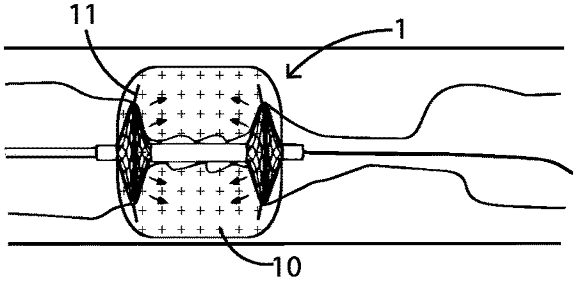

FIG. 4(*a*) shows an example of use, for comparison with the device of FIG. 4(*b*) having like parts but also having barbs 11 which contribute to an expanded electric field. The barbs 11 enhance engagement with tissue. Incorporating conductive barbs electrically connected to the electrodes enables improved tissue engagement, anchoring the device and expanding the depth of the electrical field into the surrounding tissue. As shown, the barbs 11 are best configured to extend in a direction having a radial component for penetration into tissue.

The non-conductive coupling or spacer 5 allows electrodes of the expanding bodies 3 and 4 to sit on opposite sides in the longitudinal direction of a tissue across which pulsed electric fields are applied. The shaft 6 has a proximal end which extends proximally so that a user can advance and withdraw the probe when required. The sheath 2 can be advanced over or retracted back off of the distal end of the probe providing protection during probe movement.

The term "electrode" is used to describe that portion of the probe that is configured to engage with the tissue to be treated, allowing the device to deliver electrical current through the tissue. The electrodes may, together with non-conducting parts of the expanding bodies 3 and 4, be regarded as an "engager" which engages the tissue to be treated in moving from a collapsed to an expanded state at the treatment site. These electrically connected expanding bodies are coupled non conductively to each other wherein the non-conductive coupling(s) allows elements of the expanding bodies to sit on opposing sides of a tissue or tissue across which pulsed electric fields are applied through application of independently variable voltages conducted from the drive or generator outside of the body. The entry of these electrically connected expanding bodies in a collapsed state allows their delivery to treatment sites which may have been narrowed, to varying degrees, by cancerous or non-cancerous lesions. In moving from their collapsed state to their expanded state these electrically connected expanding bodies engage tissue such as to capture tissue and facilitate a large surface contact area between the electrodes and the tissue. This expansion allows elements of the expanding bodies to sit on opposing sides of tissue across which pulsed electric fields are applied through application of independently variable voltages conducted from a generator outside of the body. A larger surface contact area between the electrodes and the tissue protects the tissue from excess current and excess heat and facilitates the delivery of a uniform electric field across the tissue.

There are two (or more in other examples) electrically connected expanding bodies colinear and in series along the probe longitudinal axis at set distances apart. These electrically connected expanding bodies are wired independently such that they are all capable of applying different voltages at different locations, for example each electrode may be individually controller and/or some may be controlled together as groups.

This embodiment has a centrally located lumen through which a guidewire can be used in order to direct advancement of the device through a partially occluded lumen. This embodiment produces an electrical field that is approximately cylindrical in shape wherein the direction of movement of electrons through the tissue and is substantially parallel with the centre line or longitudinal axis of the device and the centre line of the lumen being treated.

This probe is particularly effective when treating luminal tissue where the pre-cancerous or cancerous tissue is circumferential. The electrically connected expanding bodies may be wired such that they form two groups of bodies which when electrically active are at two set electrical potentials. These designs, when implemented with more than two expanding bodies (or "baskets") substantially increase the length of the lumen which can be treated with one application of pulses.

Other embodiments are disclosed in which the engager comprises two or more electrically connected expanding bodies which are nested or overlapping along the longitudinal axis but which remain non-conductively coupled and in the expanded state, at least, maintaining a distance between electrodes such that they can be used to apply a pulsed electrical field to the tissue. These may produce an electric field approximately cylindrical in shape wherein the direction of movement of electrons is perpendicular to the longitudinal axis.

Embodiments are disclosed (for example in FIG. 4(*b*)) in which the electrodes have tines or barbs which stick out from the edges of the expanding bodies which act to expand the electrical field penetration further into the tissue without cutting into the tissue or requiring a correspondingly larger expanded diameter. If a larger field size can be achieved with a smaller corresponding expansion diameter this may result in less vessel dissections and greater physician comfort with device usage.

Embodiments are disclosed in which the probe has shrouded needles which the user may choose to extend outward from the device body piercing into the tissue. These embodiments include versions where needle extension is user controlled or version where needle extension is preset.

Any of the above devices may further be configured to facilitate the delivery of a liquid or foam to the target tissue.

In another embodiment the expanding bodies are made from multiple different components around the circumference which are electrically insulated from each other thus allowing the physician to define that the electrical pulses are only applied to a portion of the circumference in situations where the lesion being treated is not fully circumferential.

Figure 5A:
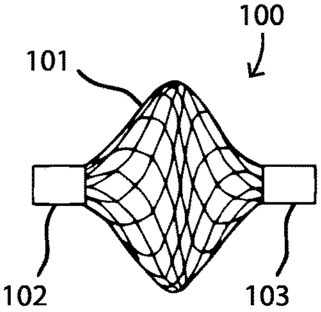
Figure 5B:
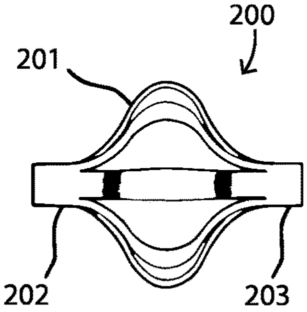
Figure 5C:
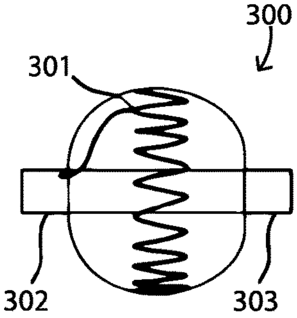

Referring to FIGS. 5(*a*), (*b*), and (*c*), expanding bodies 100, 200, and 300 are shown. The body 100 has a wire mesh 101 between couplers 102 and 103 to the elongate support. The couplers 102 and 104 are pulled together to compress the body 101 axially, thereby causing it to expand radially. This has an important effect in engaging diseased tissue in the wall of lumen, and when a pair of the electrodes are used together, they combine to grip the tissue for very effective engagement for electroporation treatment. Indeed, as also shown in FIGS. 3(*e*) and (*f*), where a spacer maintains the axial gap between a pair of electrodes, and the outer couplers pull towards the central spacer, the outer rims of the electrodes move closer together, based on the basic geometry of the electrodes. This also happens if the radial expansion is due to shape memory. This also contributes to the gripping effect.

The body 200 has a laser cut tube construction 201 between couplers 202 and 203. In its preferable implementation this entire body acts as an electrode, the electrode itself being the expanding body. This achieves excellent electrode coverage. However, in some implementations portions of the mesh may be shrouded or be of a non-conductive material to prevent them acting as an electrode. Laser tube cutting is a convenient way to provide an electrode as an expanding body. The couplers 202 and 203 perform the same function as the couplers 102 and 103.

Figure 6:
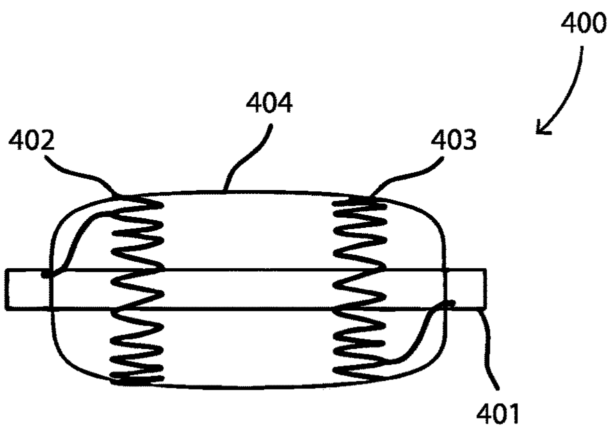
FIG. 6 is a diagram showing a single balloon acting as an expanding body to expand two separate electrodes.

The body 300 has a flexible electrode 301 printed, attached to or laid upon a balloon in a zig-zag pattern circumferentially around the balloon, thereby allowing expansion and contraction. A variation on the features of the body 300 is shown in FIG. 6, in which a body 400 has a balloon 404 with electrodes 402 and 403 at each longitudinal end, each electrode printed, attached to, or laid upon a balloon in a zig-zag pattern circumferentially around the balloon, which is mounted to a shaft 401. A balloon may have only one electrode, as shown in FIG. 5(*c*), or it may have more than 2 electrodes.

Figure 7:
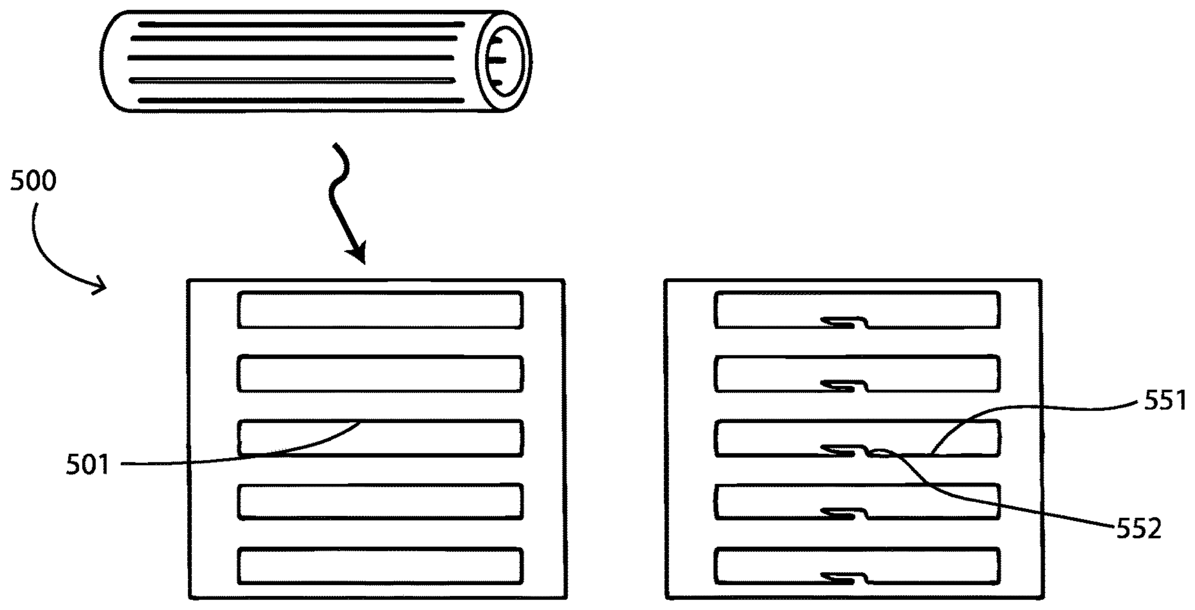
FIG. 7 shows plan views of laser cut patterns (not to scale) without barbs (left) and with barbs (right), which demonstrate how barbs are implemented as part of the laser cutting process, FIGS. 8(*a*) and (*b*) are illustrations showing that a device of the invention can open to different degrees, FIGS. 9(*a*) to 9(*c*) are three diagrams showing a probe with radial needle electrodes in its collapsed state (a), inflated state (b) and inflated state with needle electrodes extended outward (c), FIGS. 10(*a*) and (*b*) show a side view and an end view respectively of a device in which the electrically connected expanding bodies are partially or completely overlapping each other along the device centre line and with different radial dimensions.

As noted above barbs or other features for penetration of tissue for enhanced anchoring in the tissue may be provided, and as shown in FIG. 7 a laser cut pattern 500 has electrode lengths 501, and on the right-hand side a laser cut pattern has lengths 551 with barbs 552.

Figure 8A:
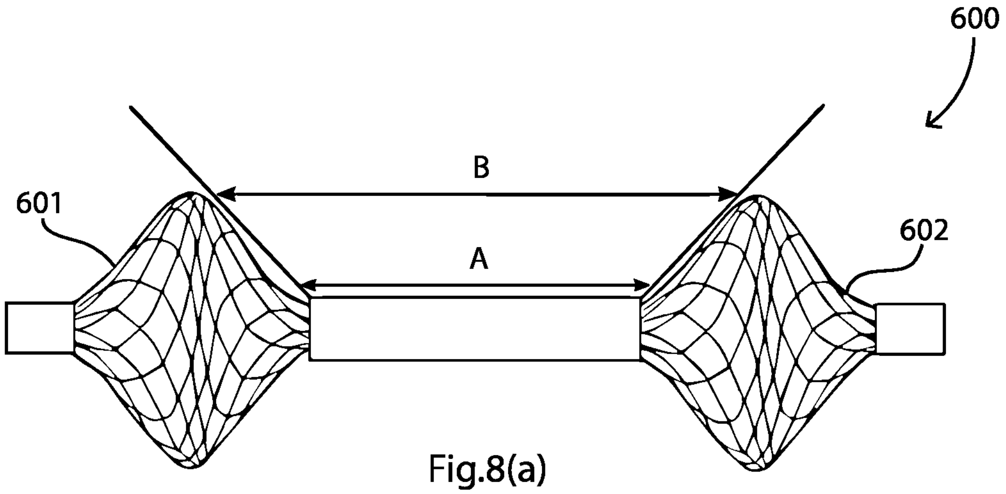
Figure 8B:
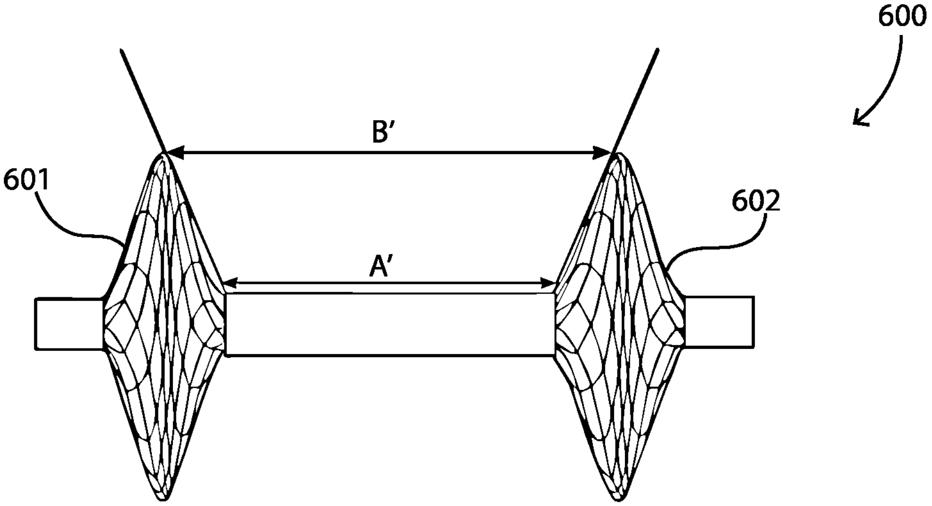

FIGS. 8(*a*) and (*b*) show how a probe 600 can have all-electrode mesh expanding bodies 601 and 602 which can open to different degrees, either user-mediated or dictated by tissue stiffness. Feedback on the tissue impedance between the electrically connected expanding bodies could be used to modify the input voltage so that the maximum volume of tissue experiences and electric field within the relevant voltage/cm window. Alternatively, the feedback may be haptic for the user who then stops sliding the handle, thereby preventing the device from causing a dissection in the lumen. As illustrated in FIGS. 8(*a*) and (*b*) the annular boundaries of the volume between the bodies 601 and 602 have different angles with respect to the longitudinal axis and different maximum lengths B and B', and indeed different minimum lengths A and A'. The smaller dimension B' shows that the ends of the meshes 601 and 602 which face each other converge to help cause a pinching effect to grip diseased tissue which extends inwardly into the lumen (see also FIGS. 28(*a*) to (*c*).

Needle Electrodes

Figure 9A:
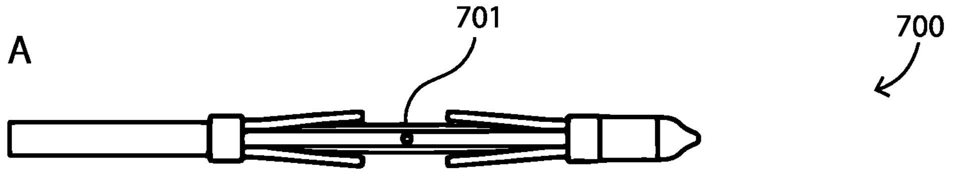
Figure 9B:
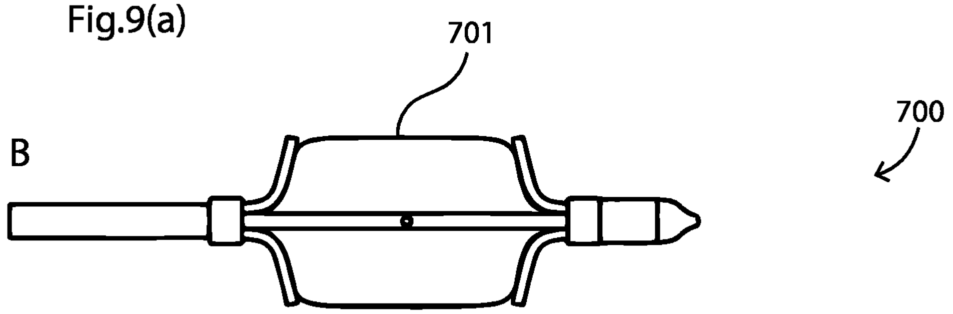
Figure 9C:
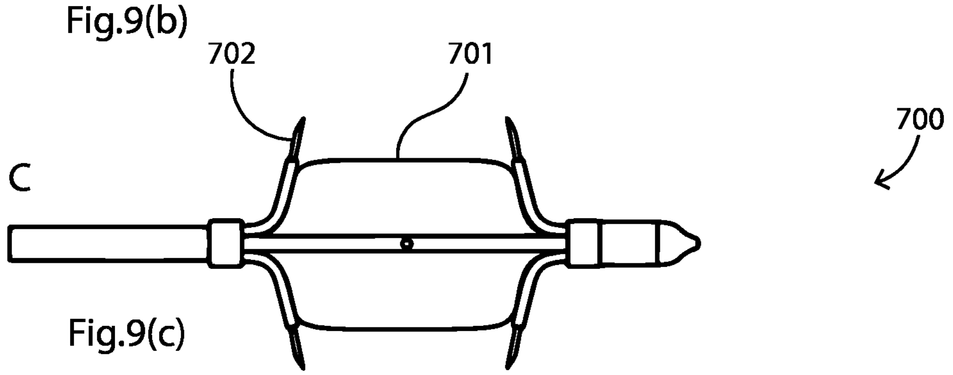

There may be any desired configuration of electrodes, and indeed the electrodes may include needle extensions which extend with a radial directional component for improved physical anchoring in tissue and greater penetration of the electrical field. As shown in FIGS. 9(*a*), (*b*), and (*c*) a probe 700 has a balloon 701 at each end of which there is a needle 702 which extends from a sleeve under action of an actuator comprising of one or more push/pull wires coupled to the bodies that either hold the circular array of needles or, in an alternate construction, is the tube from which the needle profiles are cut.

The expanding body may in some examples be constructed of a balloon catheter around which lie multiple needles which lie parallel to the catheter centreline and are enclosed within "shrouding" polymer tubes covering their sharp tips. These needles partially cover one first proximal end of the balloon and a second distal end of the balloon with their needle tips oriented toward the middle portion of the balloon, see FIG. 9 (*c*). These needles are preferentially manufactured from a shape memory alloy, for example Nickel Titanium (NiTi), or another self-expanding material potentially, to take advantage of both the high levels of strain which these materials can undergo before undergoing plastic deformation and the shape memory capabilities it exhibits. Alternative embodiments might have needles made from 304 stainless steel or other materials typically used for hypodermic needles. Any of these materials may be platinum or gold plated. Further, these sets of needles may be attached together at their butt or along their shank such that the needle sets can be moved together as a single unit. In one configuration these needles have been laser cut from a single metal tube and subsequently polished to somewhat round the laser cut profile thus reducing the number of distinct parts required to construct this device.

During usage inflation of the balloon re-orients the needle tips so that they are now oriented outwards radially from the catheter shaft, see FIGS. 6 and 9. Actuation of a slider, push button or thumbwheel moves these needles forward in their respective tubes and thus radially outward into the surrounding tissue. Electrical pulses can now be applied between the two sets of needles to induce Reversible Electroporation (RE) or Irreversible Electroporation (IRE) in the tissue between and immediately surrounding the electrode needles as desired. After application of the desired treatment to the target area the user retracts the needles and deflates the balloon. The needles return to their default shape set shape which allows them to conform to the outside of the deflated balloon. The device may now be moved to a new treatment area until all tissue that requires treatment has been addressed. The needles help to deliver the electroporation energy deeper into the tissue without over distending/compressing the tissue. These needles are sufficiently long to allow them to be deployed from the device to a depth appropriate for treating the pre-cancerous or cancer being target, perhaps 2-8 mm depth.

When inflating the balloon to re-orient the needles radially some tissue may be stiff and thus cause the needles to be pushed out of their intended and desired circumferential spacing. In such circumstances inflating the balloon fully to push back tissue, deflating partially to allow the needles spacing return to that intended and reinflating to the target balloon diameter may improve the needles spacing. Since each set of needles acts as a unified electrode at a given voltage, the electrical field is not sensitive to the variable needle spacing around the circumference caused by stiff tissue.

In one configuration the needles when emerging from the shroud tubes are substantially perpendicular to the centre line (longitudinal axis) of the catheter. In another configuration, the needles emerge with an interior angle formed between the needle tip centre line and the catheter centre line that is less than 89°, such angle being intended to modify the resulting electric field such that it is more uniform between the two electrode sets as each electrode sets needles are further apart circumferentially the further they extend from the central axis.

Sample Procedure of Device Use

- The physician retracts the protective sheath until it is distal to the balloon and needle electrodes.
- The physician inflates the balloon which causes the polymer tubes and thus contained needles to become radially oriented.

Actuation of a slider/thumbwheel/button on the handle moves the needle sets forward in the polymer tubes causing them to extend outward into the surrounding tissue.

Electrical pulses are then relayed between the extended needles such that the tissue between needles at one end of the balloon and the other end are effectively reversibly electroporated (RE).

The needles are then retracted, balloon deflated and the device can be moved to treat another location.

Figure 10A:
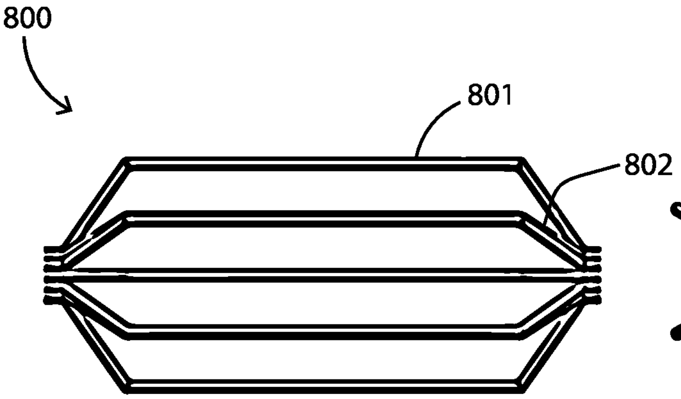
Figure 10B:
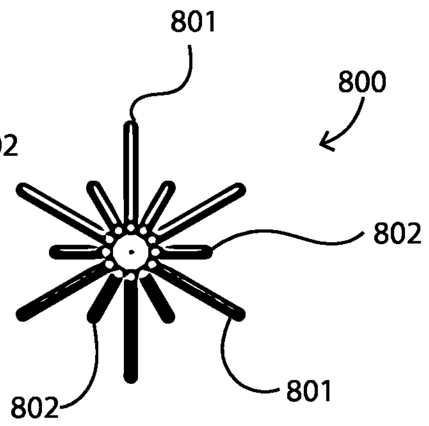

FIGS. 10(*a*) and (*b*) show a probe 800 in which the electrodes are partially or completely overlapping each other along the device centre line (longitudinal axis). This is achieved by electrodes which are tapered outwardly, then along parallel to the axis, and then inwardly. Electrodes 801 have an axial portion which is further from the axis than electrodes 802. In this case each alternate electrode is of different radial dimension and electrical charge in use, but the pattern may be different, such as a bias to a greater radial dimension on one side of the axis than the other.

Figure 11:
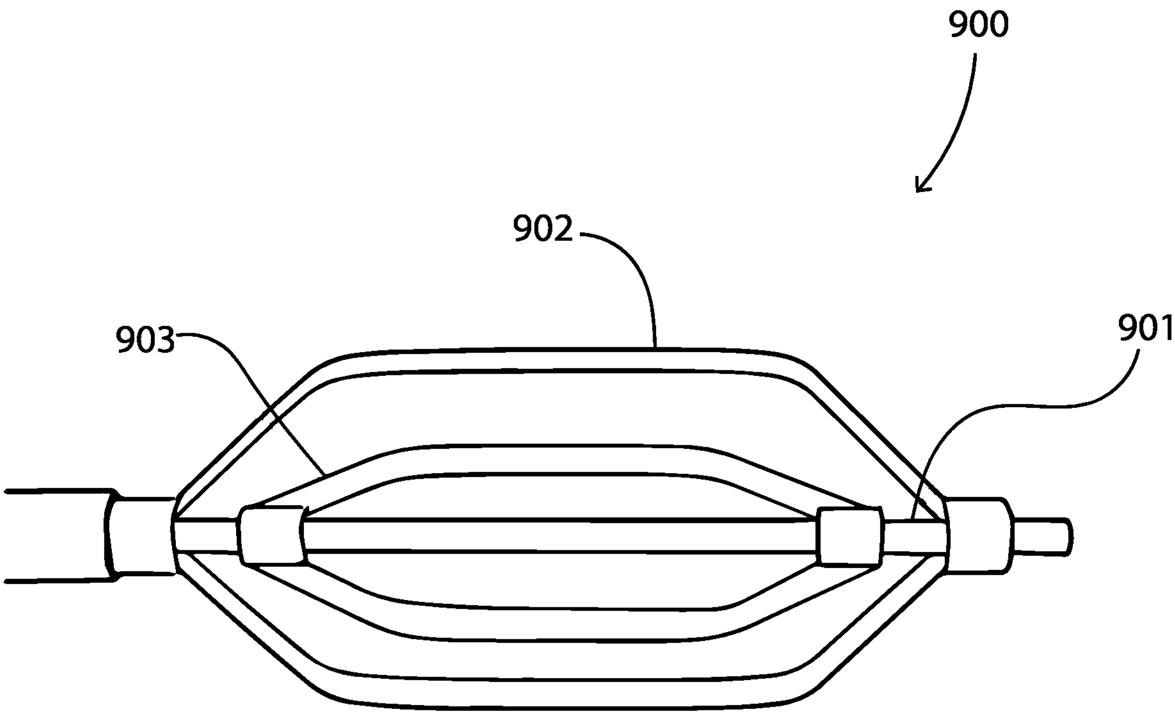
FIGS. 11 and 12 are side views showing an expanded basket of another probe of the invention, FIGS. 13(*a*) and (*b*) are a perspective view and a side view respectively of an alternative probe, in this case having three expanding bodies.
Figure 12:
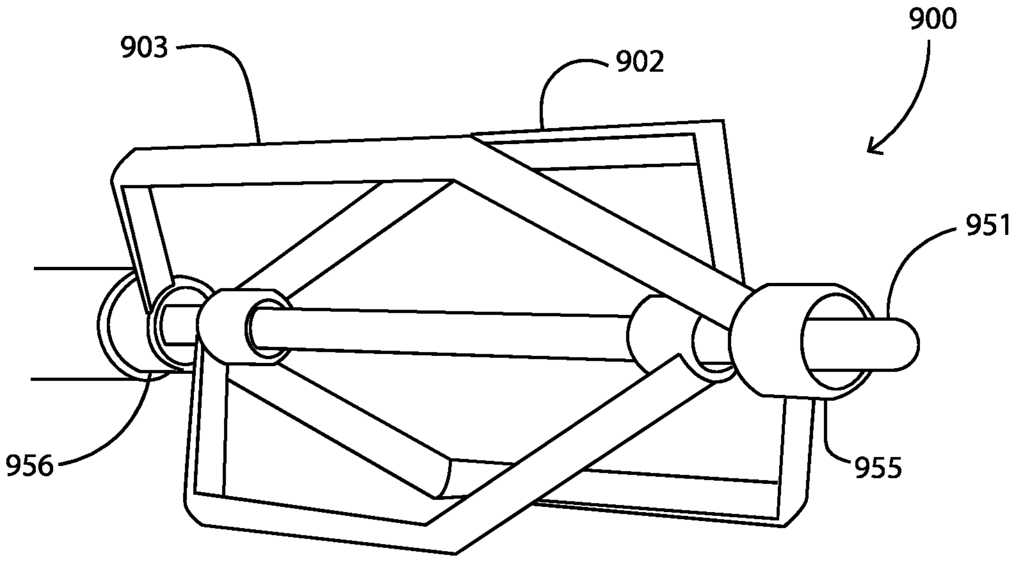

On the other hand, FIGS. 11 and 12 show an expanding body 900 with a central column 901 supporting two separate laser-cut electrodes, 902 and 903, which expand radially to the same degree and are spaced apart on the circumference.

In most examples of the invention the electrodes are spaced axially, but as illustrated in FIGS. 10 to 12 they may be spaced circumferentially.

Figure 13A:
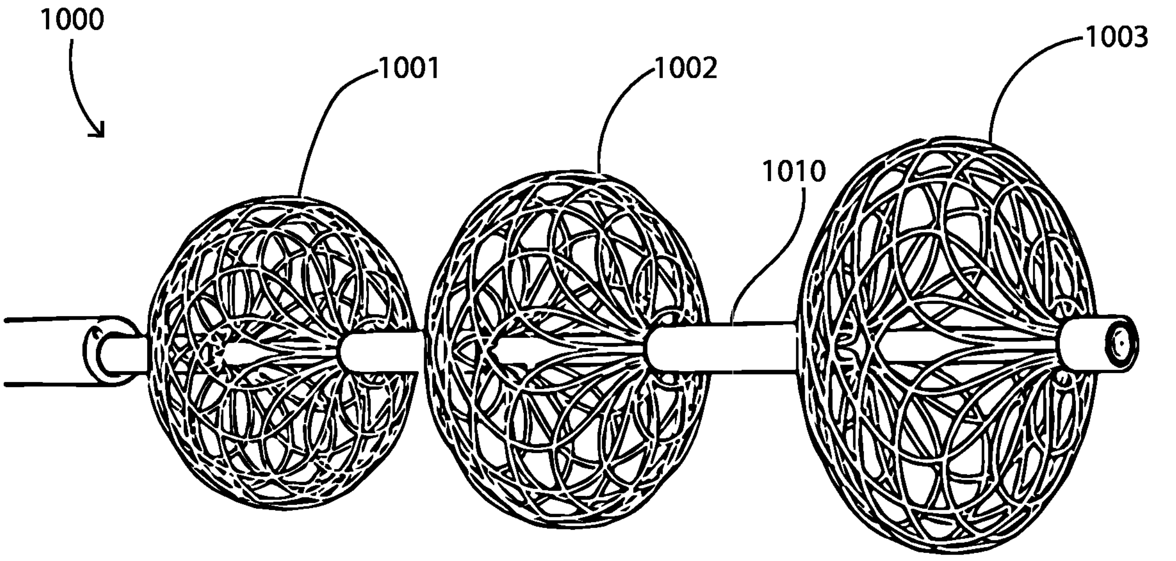
Figure 13B:
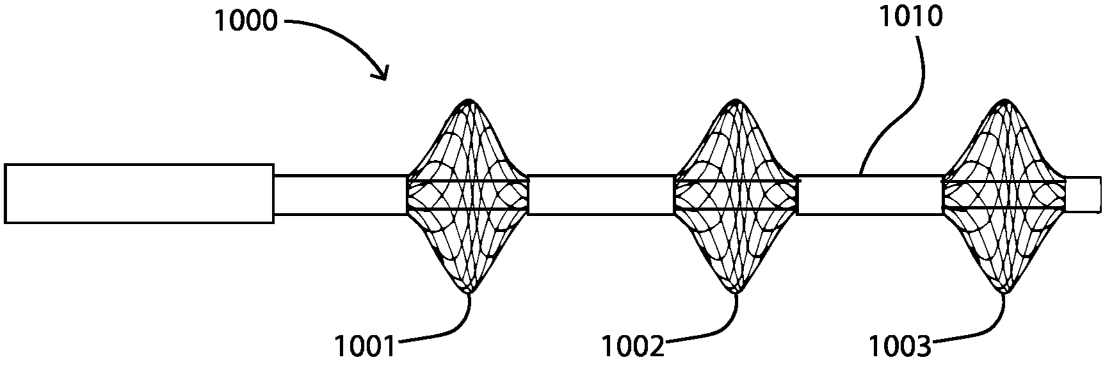

Turning again to a probe with electrodes spaced axially, FIGS. 13(*a*) and (*b*) show a probe 1000 with three longitudinally spaced expanding bodies 1001, 1002, and 1003 supported by a shaft 1010. It will be appreciated that any desired number of electrodes, of any of the types described may be mounted to the shaft.

Figure 14:
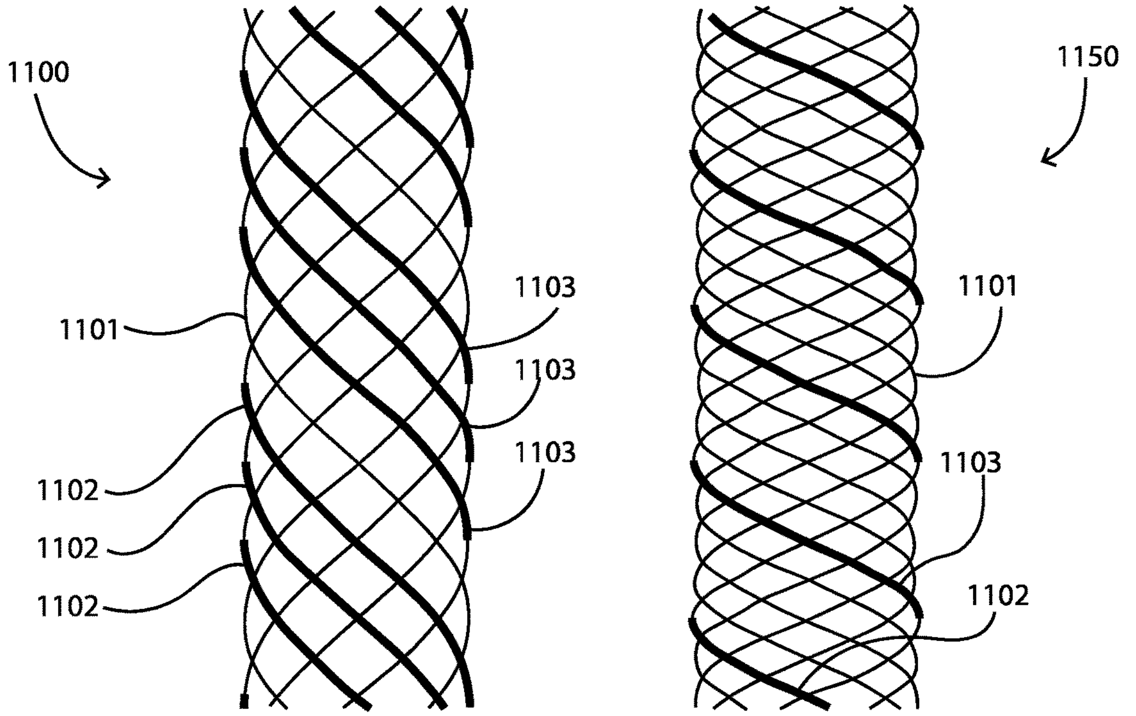
FIG. 14 shows a probe in which the expanding body of the device is a mesh made from a non-conductive weave with conductive material interwoven at regular intervals; this is shown in two possible variants demonstrating how the number and position of conductive elements may be varied.
Figure 15:
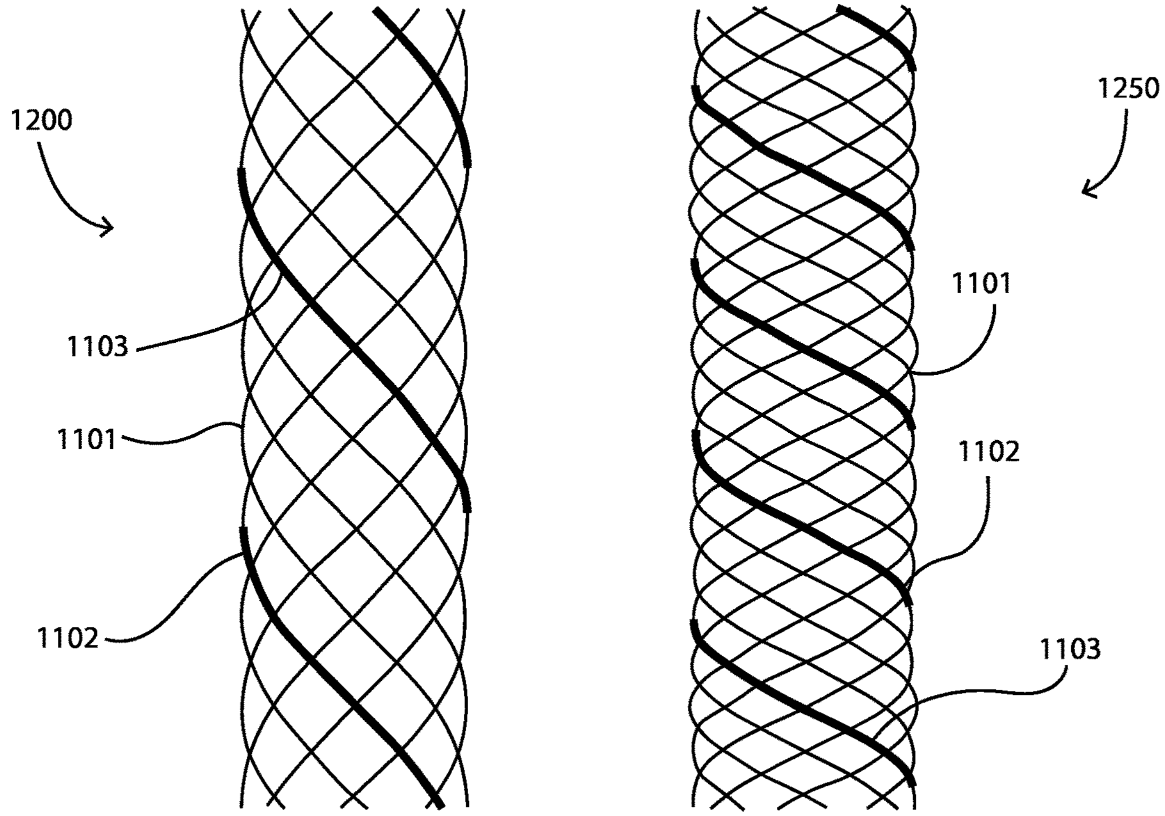
FIG. 15 shows probes akin to those of FIG. 14, but which have been compressed axially to half the original length; this demonstrates how the conductive strands remain parallel to each other and do not come into contact as a result of the compression.

FIGS. 14 and 15 show examples of expanding bodies with both electrodes and non-conductive strands, in this case braided meshes, identified as 1100, 1150, 1200, and 1250. Each has a combination of non-conductive strands 1101, strands 1102 of one polarity and strands 1103 of the opposite polarity. As is clear from these diagrams any desired combination of numbers, of distribution, and of thickness of strands is possible at manufacture. The braided mesh used to construct such a device would ideally be highly constrained with each strand passing in series over one strand and under the next thus ensuring that the non-conductive strands 1101 sufficiently constrain the conductive strands 1102 and 1103 from touching under most circumstances. Due to the well constrained nature of the device short inter electrode distances can be achieved while allows use of lower voltages to achieve similar levels of electric field strength in the tissue. This could allow the achievement of IRE in vessels where this previously was not achievable due to the input voltages required on current devices and the associated muscular and pain responses seen with such large input voltages.

Figure 16:
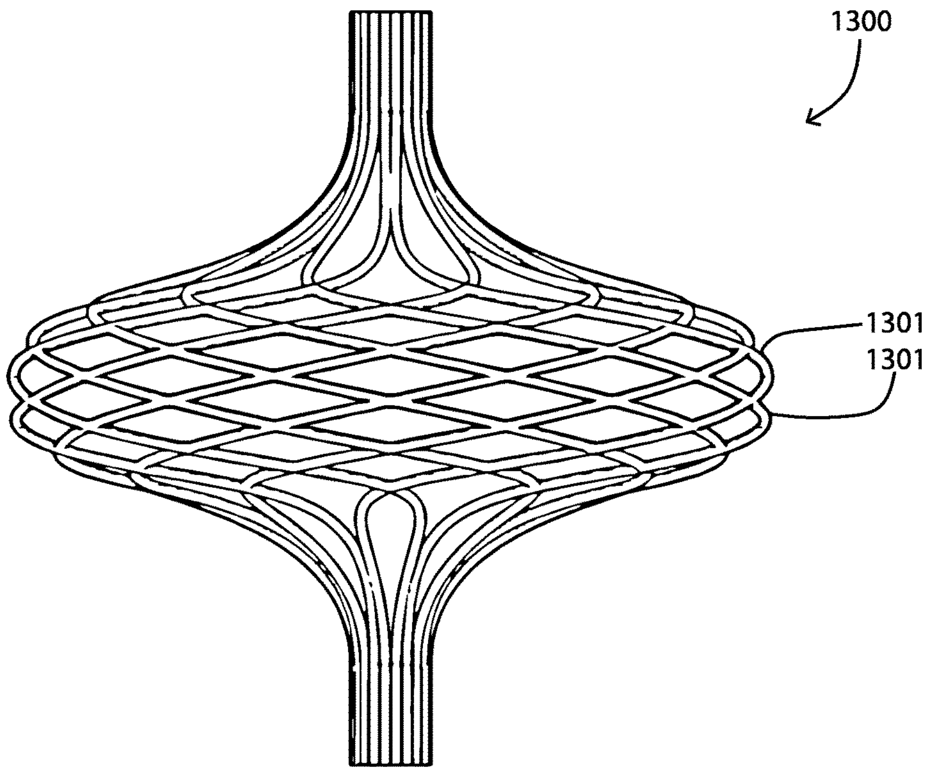
FIG. 16 shows a side view of an expanding body in which there are 20 strands, and they are all of the same diameter.

FIG. 16 shows an expanding body 1300 in which there are 20 strands 1301 and they are all of the same diameter and they are all conductive. This is provided primarily as a comparator for FIG. 18.

Figure 17:
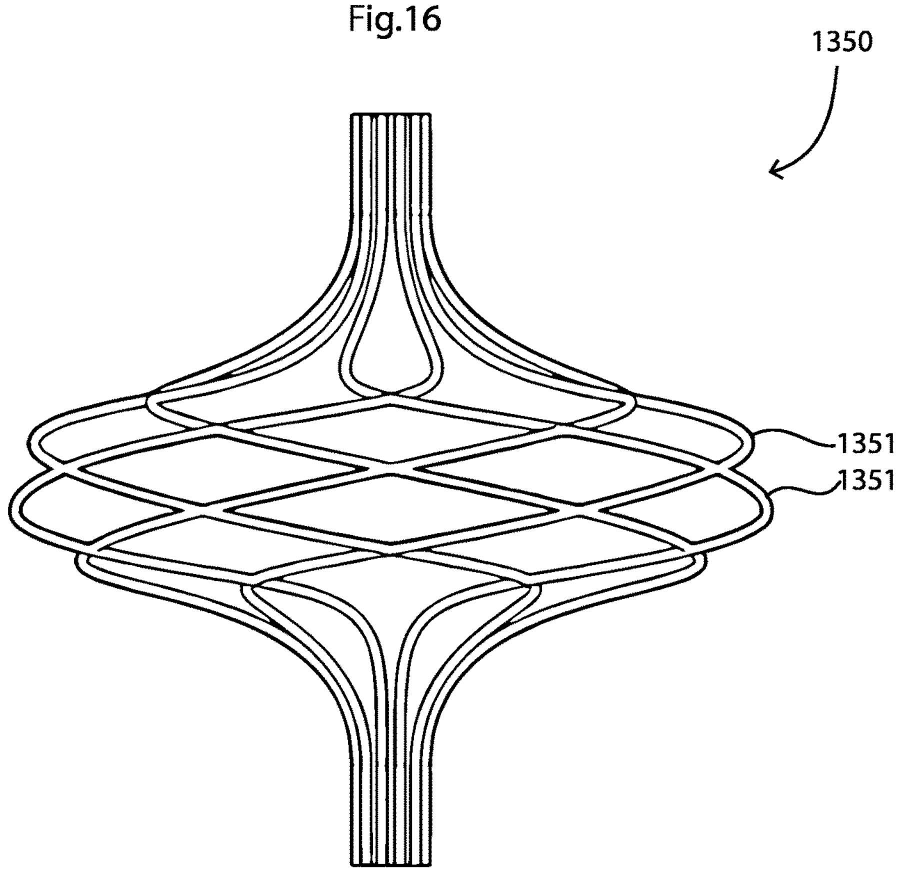
FIG. 17 shows a side view of an expanding body having 12 strands, again of the same diameter.

FIG. 17 shows an expanding body 1350, having 12 strands 1351, again of the same diameter and again all conductive. Again, this is provided primarily as a comparator for FIG. 18.

Figure 18:
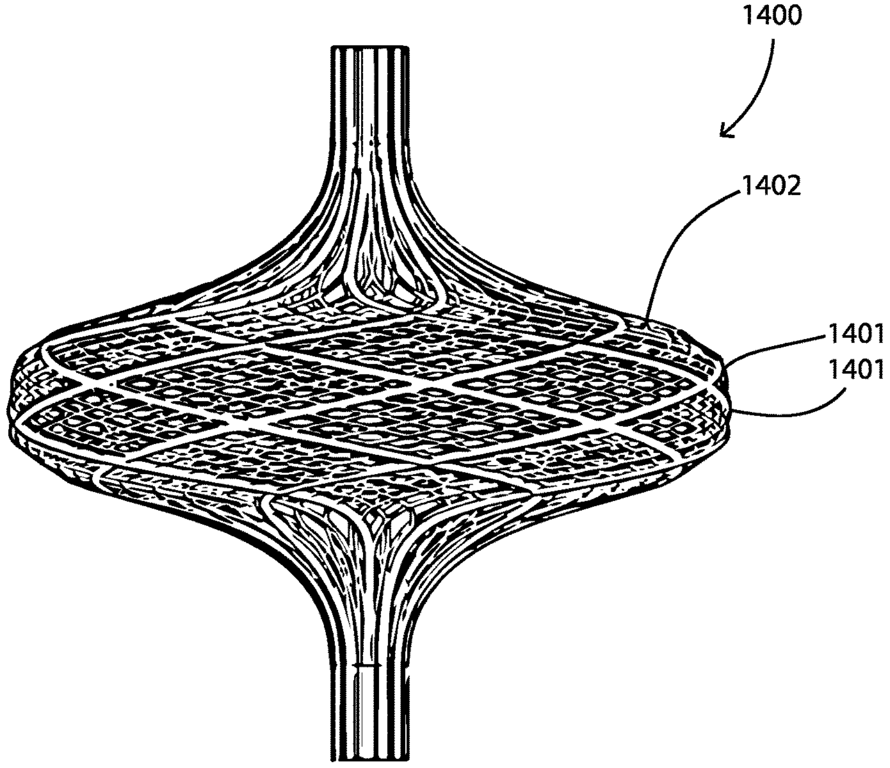
FIG. 18 shows a side view of an expanding body with 12 strands of medium diameter and 36 strands of smaller diameter providing smaller mesh gaps, FIGS. 19(*a*) and (*b*) show a side view of a series of expanding bodies spaced reliably apart by balloon spacers with short inter-basket distances, FIGS. 20(*a*), (*b*), and (*c*) show side views at three stages of use of a device having two centrally biased expanding electrode meshes with an expanding balloon barrier between them which limits the shortest inter-electrode distance the tissue will experience during pulsing.

FIG. 18 shows an expanding body 1400 with 12 strands 1401 of medium diameter and 36 strands 1402 of smaller diameter providing smaller mesh gaps, all of the wires being conductive as electrodes. The resulting arrangement has a combination of the enhanced strength imparted by the larger diameter wires, the smaller mesh gap size achievable with the smaller diameter wires and wraps down under smaller end collars than could be achieved with an expanding body with similar mesh gap sizes and not using multiple wire diameters in its construction.

Figure 19A:
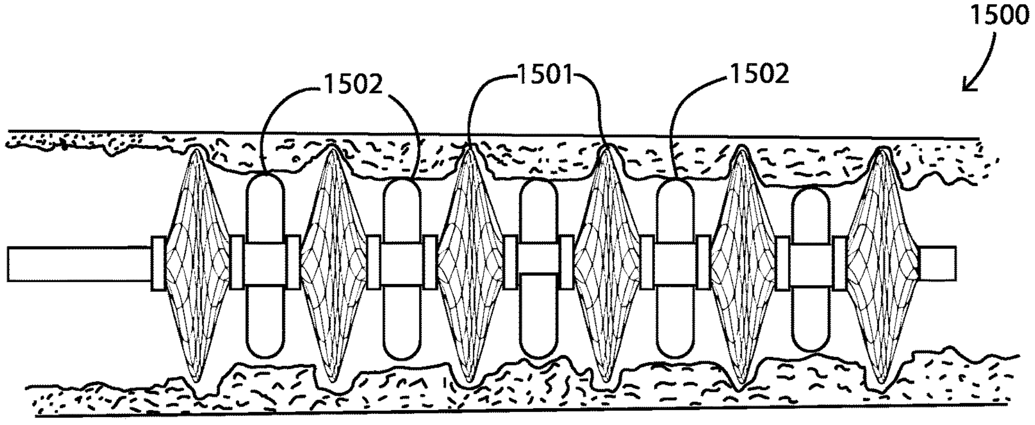
Figure 19B:
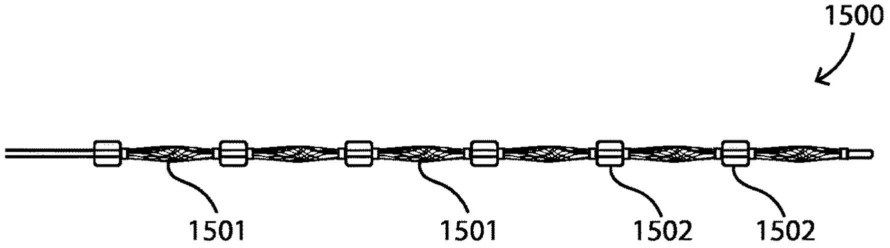

FIGS. 19(*a*) and (*b*) show a probe 1500 with a series of six baskets 1501, each basket being separated from the basket beside it by a catheter balloon 1502 to ensure a repeatable inter-basket distance independent of the target vessel diameter or any relative movement between electrode device and vessel. Shorter inter-basket distances can be achieved with the balloon spacers, 1502, than without as they decrease the risk of basket-to-basket contact, which would result in a short circuit and resultant damage to the attached pulse generator. Shorter basket distances are desirable in order to allow application of IRE treatment to tissue without the high voltages current devices are required to deliver due to their larger inter electrode distance.

Figure 20A:
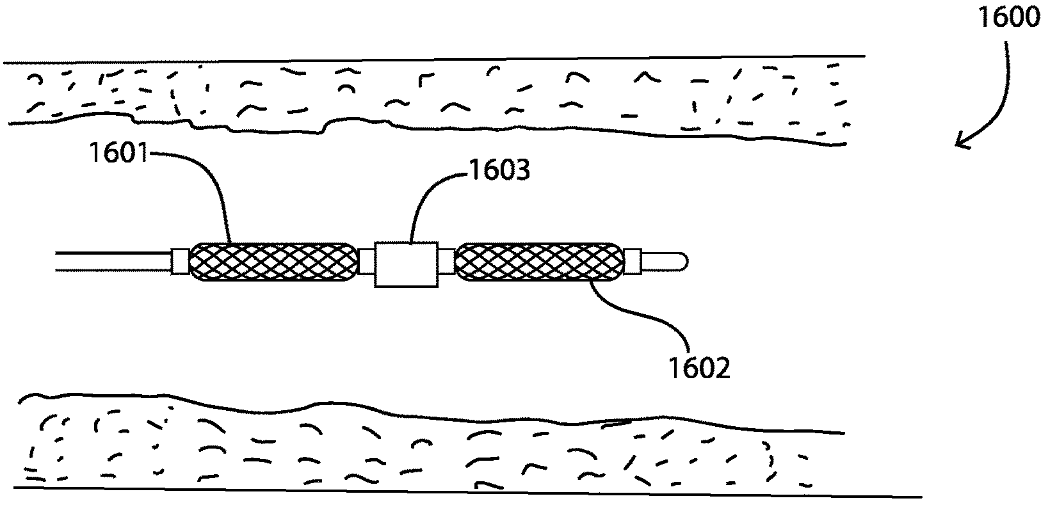
Figure 20B:
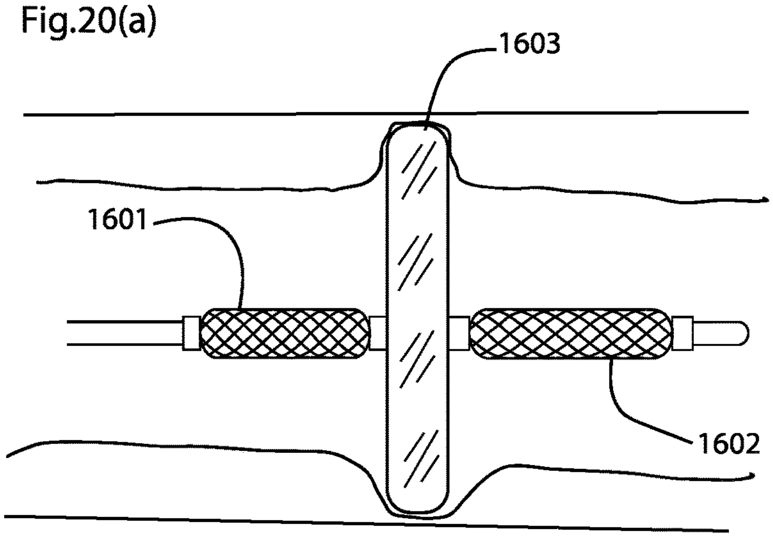
Figure 20C:
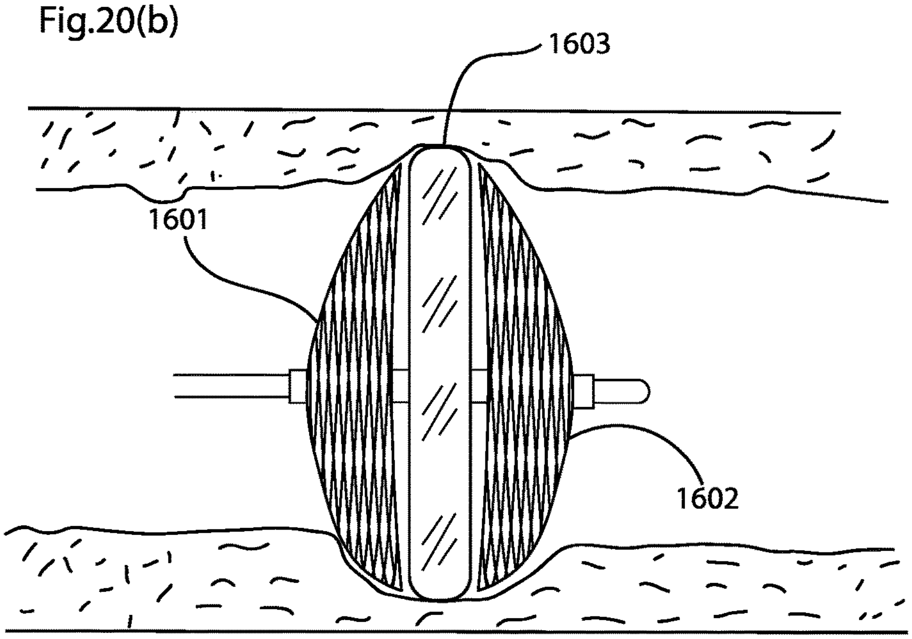

FIGS. 20(*a*), (*b*), and (c) show a series of three stages of opening a probe 1600 having proximal and distal baskets 1601 and 1602 and an expanding support 1603 in-between them. The baskets, 1601 and 1602 have been heat set to have a shape biased towards the centre between the baskets, which ensures that each electrode contacts the vessel close to the edge of an expanding support, 1603, which ensures a reliable minimum inter-electrode distance.

Figure 21:
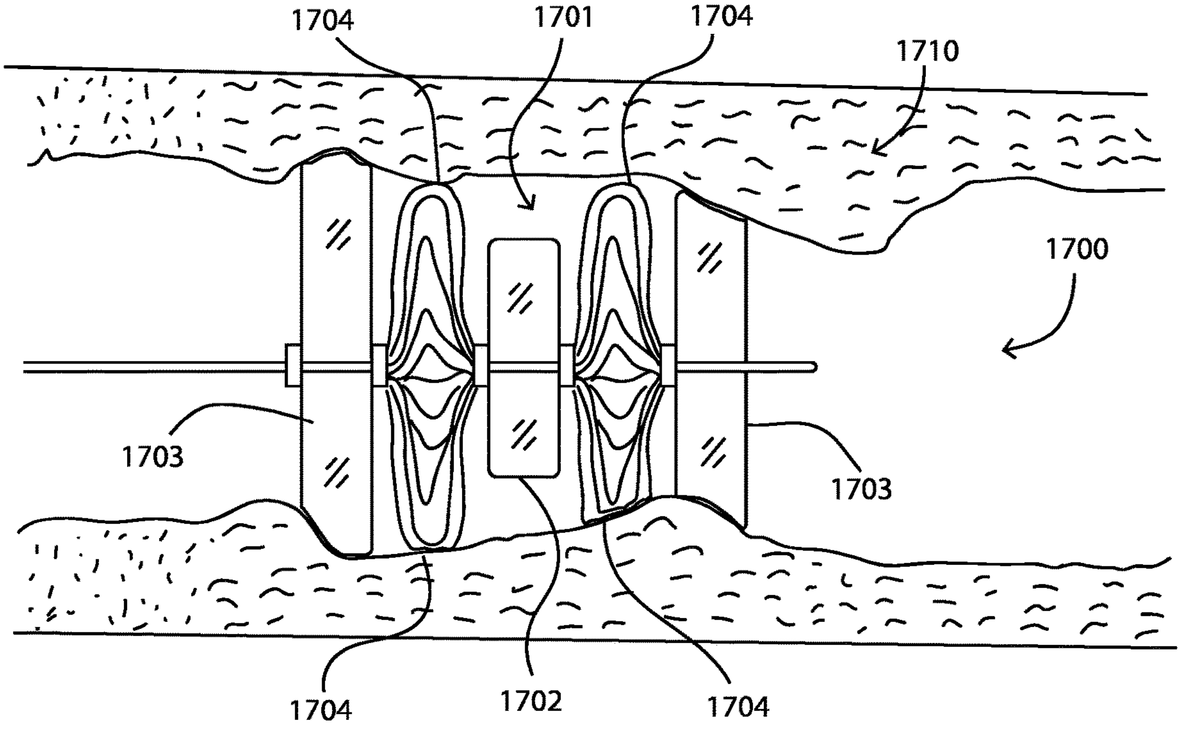
FIG. 21 shows a probe with a single pair of expanding baskets, and a separator balloon in-between and one proximally of the proximal basket and one distally of the distal basket, in which the central separator balloon has a smaller radial extent than the other two balloons.

FIG. 21 shows a probe 1700 having two expanding electrode bodies, 1704, bracketed by two expanding balloons 1703, intended to create an enclosed area into which a fluid agent such as a foam agent can be delivered. In addition, the space 1701 between the balloons 1703 has another expanding balloon, 1702, intentionally designed to be smaller in diameter than the target vessel and serving the purpose of decreasing the volume of the enclosed area, thus allowing foam to sufficiently fill said volume. Pressured delivery of foam into the enclosed volume may enhance uptake of foam and its active constituents into the surrounding target tissue.

In this example the purpose of the external balloons 1703 is to seal off the space between the expanding electrode bodies, and that of the internal balloon 1702 is to reduce the volume of space between the expanding electrode bodies and to keep a fixed distance between said electrode bodies. This arrangement allows very effective filling of the space between the expanding electrode bodies with a foam or other solution to adjust the conductivity to help ensure adequate electroporation. This also reduces the voltage required to generate an adequate electrical field.

It should be noted that the electrical field is controlled by the width of the contact area between the expanding electrode bodies 1704 and the tissue; the narrower the expanding electrode bodies the narrower the depth of field radially and vice versa.

Figure 22:
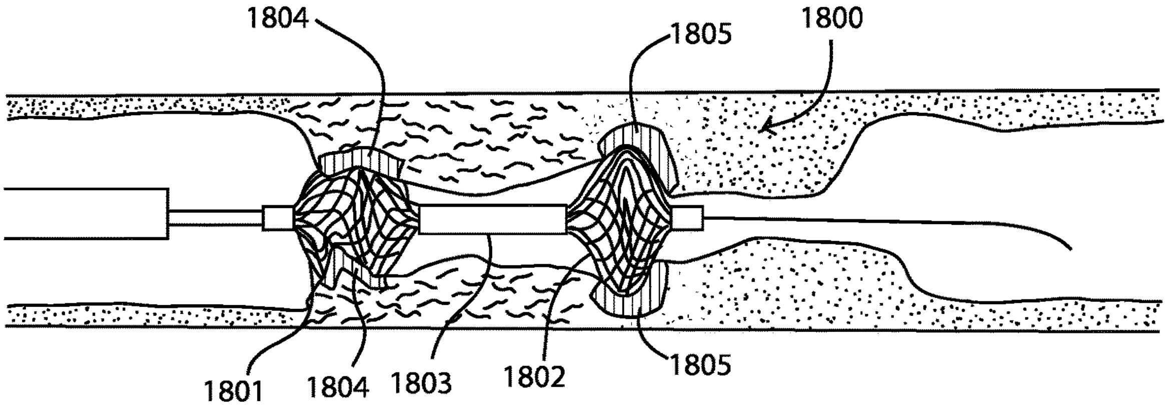
FIG. 22 is a diagrammatic side view of a probe in use, in which the baskets deform to different extents to the shape of the tissue surrounding them, according to user actuation at the proximal end.

FIG. 22 shows a probe 1800 with two longitudinally spaced apart electrodes which themselves form expanding bodies 1801 and 1802 separated by a spacer 1803 which defines the inter-electrode distance between said baskets. The basket 1801 is complying with surrounding hard tissue 1804, whereas the basket 1802 is deforming soft tissue 1805 at its location. Both baskets have identical or almost identical constructions. However, actuation of both baskets is linked such that the user applied force at the handle is translated into each basket expanding to the degree achievable with said force. This is achieved through mechanical or pneumatic linkage of the basket movement. The user can feel the resistance to expansion caused by actuating the couplers to move axially to expand the electrodes.

In some preferred examples each electrode is configured to exert a radial force to dilate soft, compliant tissue yet conform to harder stenosed tissue without causing dissection or perforation, said force being in the range of 0.1 $N/mm^2$ to 1 $N/mm^2$.

Figure 23:
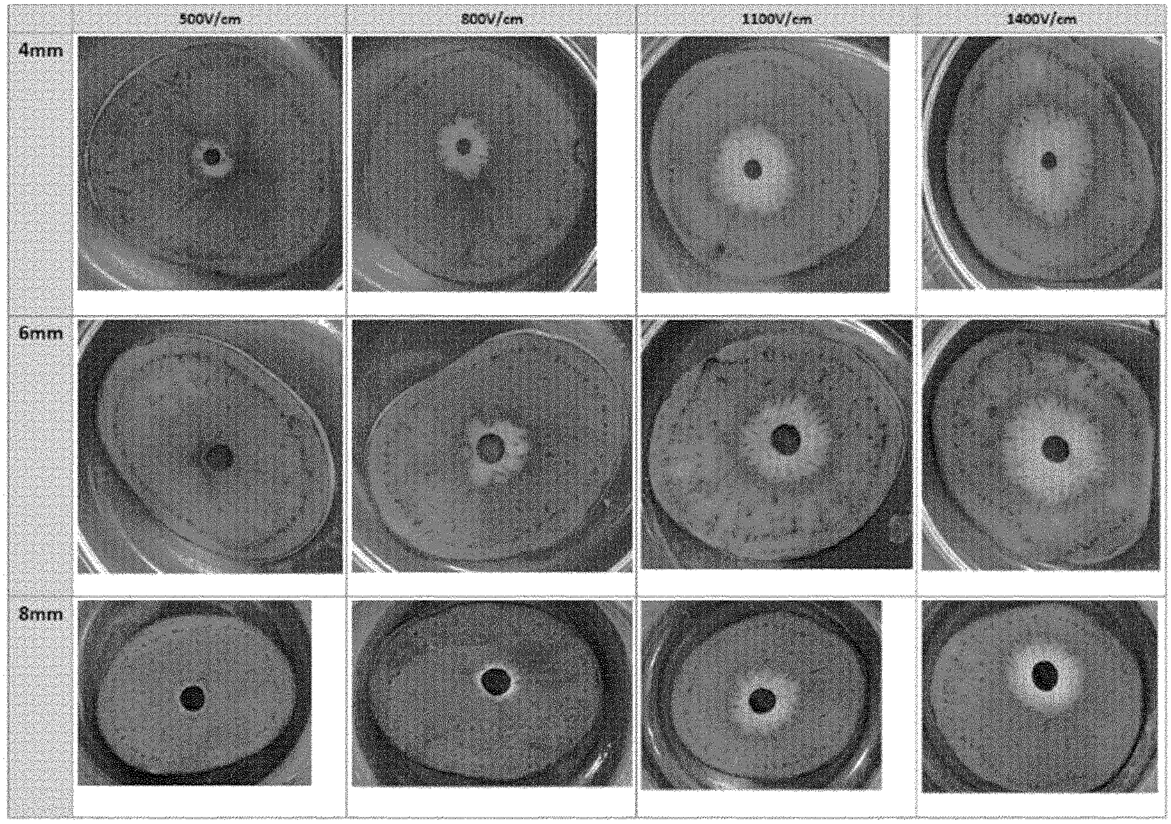
FIG. 23 is a set of twelve images showing the results of tests, arranged as three rows of four images for 4 mm, 6 mm, and 8 mm diameters respectively, showing the effect of electroporation with expanding bodies of type.

FIG. 23 is a set of twelve images showing the results of tests, arranged as three rows of four images for 4 mm, 6 mm, and 8 mm diameters respectively, showing the effect of electroporation with expanding bodies. All images were generated with a single prototype device of the design illustrated in FIG. 22 deployed in the well understood potato model for electroporation. Use of 2,3,5-Triphenyltetrazolium chloride (TTC) at a 0.5% concentration for staining of the "electroporated potato's" allows direct visualisation of the extent to which the potato cell walls have been disturbed by the applied electric field pulses. This prototype had a fixed distance between the electrodes. It can be seen that with increasing input voltage and thus increasing electric field strength, left to right, the depth of electroporated plant tissue increases for each given channel diameter. Moving from the 4 mm channel to 6 mm and 8 mm diameter channels demonstrates that although the electroporated cross-sectional area at different diameters can be approximately similar in size it extends into the surrounding tissue to a lesser extent when the diameter the pulses are being delivered at is larger. This means a device of this design may be capable of using in highly occluded lumen, where the intent is to treat to great depth, and less occluded lumen, where the desire is to treat the lumen surface without extending into tissues beyond the surface.

Figure 24:
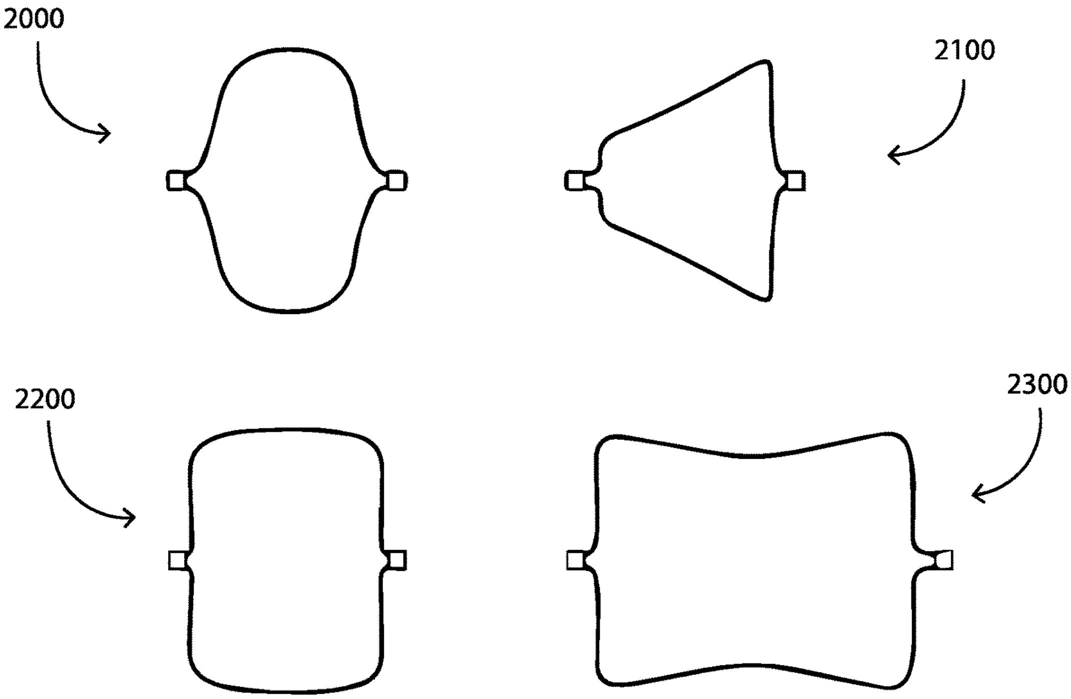
FIG. 24 is a set of diagrams illustrating the overall outer envelope of expanding bodies of the invention, namely oval, conical, square, and "dog bone"

FIG. 24 is a set of four diagrams illustrating the overall outer envelope of expanding bodies of devices of the invention, namely oval 2000, conical 2100, square 2200, and "dog bone" 2300. The oval body shape is similar to that illustrated in FIG. 22. These devices may be used in vessels of greatly varying diameter and morphology, as an oval body expands in a vessel the electrodes contact the vessel to be treated at a point some distance from the spacer which defines the inter-electrode distance, this distance will vary depending on the vessel size, tissue flexibility and shape. With two electrodes in a row the effective electrode distance, i.e the distance between where each electrode contacts the tissue may potentially be much greater than the intended inter-electrode distance as defined by the length of the spacer 1803. This increase in distance will thus result in a lower v/cm for application of treatment and potentially less efficacious treatment. This can be mitigated by having other heat set or mechanically defined shaped for the expanding electrodes like those shown. The shape 2100 is particularly preferred for treatment of tissue which projects into the lumen in a discrete manner, as two of the electrodes 2100 having their wider ends facing each other are particularly suited to pinch such tissue.

Figure 25:
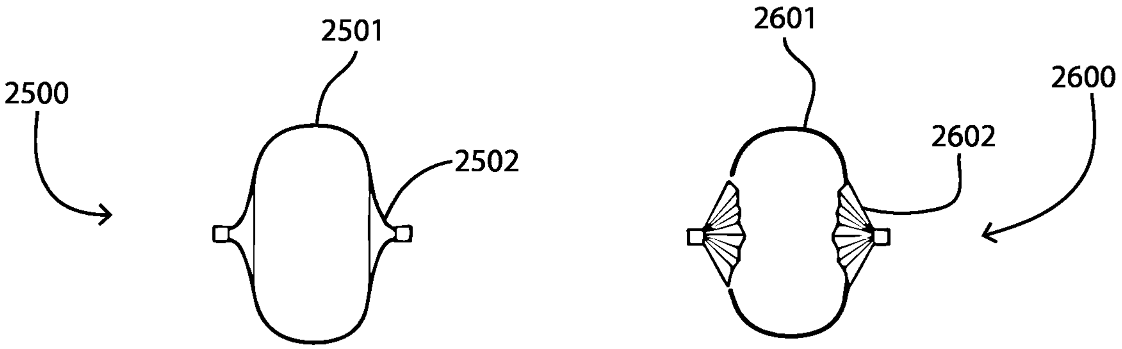
FIG. 25 is a pair of diagrams of devices showing locations of insulated wires to ensure insulation of the axially separated bodies.

FIG. 25 is a pair of diagrams showing devices 2500 and 2600 with expanding bodies 2501 and 2601 which are insulated at their proximal and distal ends to prevent the potential for the occurrence of a short circuit. The probe device 2500 demonstrates a basket 2501 having strands at each sided which are coated with an insulating material. One way this could be achieved would be through a dip coating manufacturing step. The probe device 2600 demonstrates a basket 2601 over which lays an insulative overlay that expands with the basket. In most situations they only need to extend from the axis for some of the radial distance on the inside end of the expanding body. It will be appreciated that the use of a balloon in-between helps to ensure a repeatable separation and minimises requirement for insulating wire strands.

Figure 26:
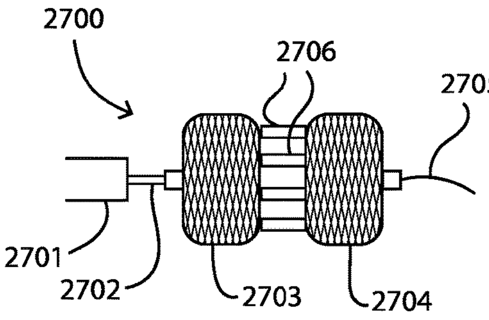
FIGS. 26 and 27 are side views of a device in which a spacer comprises a number of spacer elements parallel to the longitudinal axis, FIGS. 28(*a*), (*b*), and (*c*) are a series of side views showing operation of the device of FIG. 1 for treatment of a nodular pre-cancerous tumour in the bowel.

FIG. 26 shows a probe 2700 with a catheter 2701, an elongate support 2702, a proximal expanding body 2703, a distal expanding body 2704, and a guidewire 2705. In this case the bodies are separated by eight parallel spacer members 2706 equally circumferentially spaced apart around the longitudinal axis.

Figure 27:
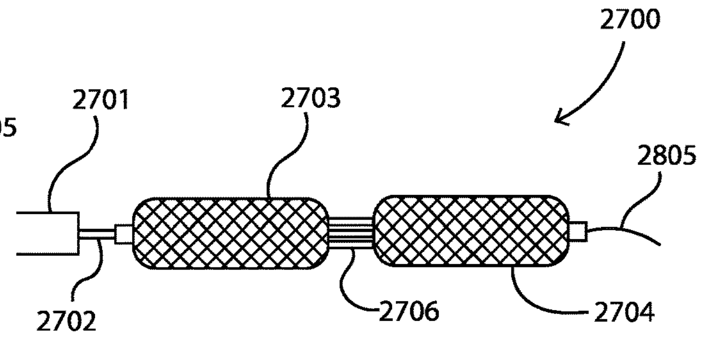

FIG. 27 shows the probe 2700 with the expanding bodies 2703 and 2704 stretched longitudinally and narrower. This shows that the spacer members 2706 track the change in radial dimension. When the meshes are expanded, the spacer helps to maintain separation even at the furthest positions from the axis. In some examples there may be from two upwards of spacer elements, the number being chosen to help achieve consistent maintenance of a desired separation between the expanding bodies at both the longitudinal axis and radially outwardly from it. This results in less variability in the distance between the contact points of each basket electrode when the device is used in different diameter vessels.

These probes are advantageous in that the insulator lengths define the effective electrode distance and thus the distance for communication of electrical pulse waves can be considered fixed. These probes fix the effective electrode distance while allowing for some tissue between the electrodes to remain in-situ.

Figure 28A:
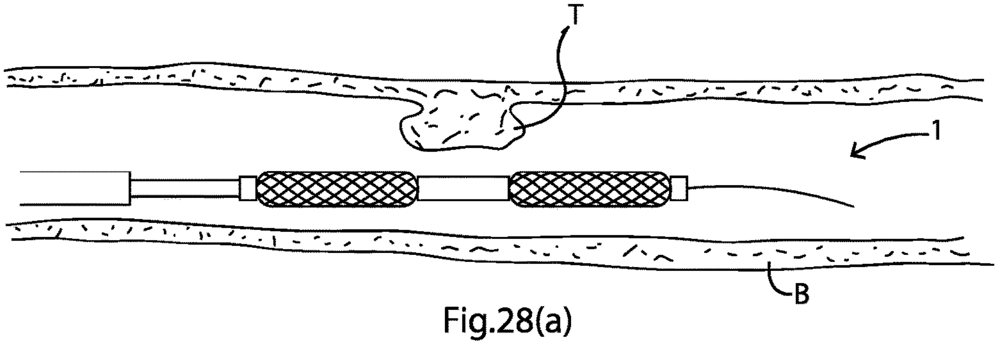
Figure 28B:
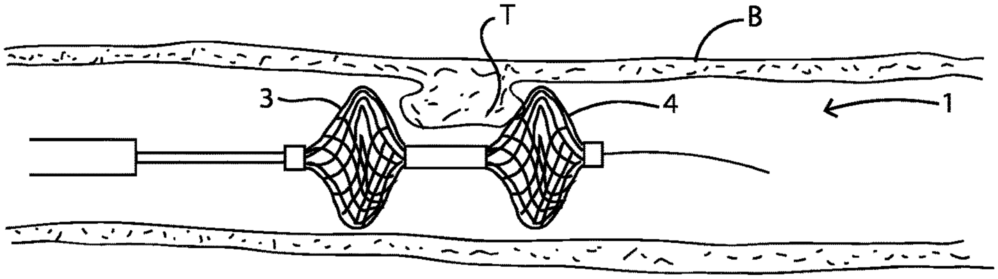
Figure 28C:
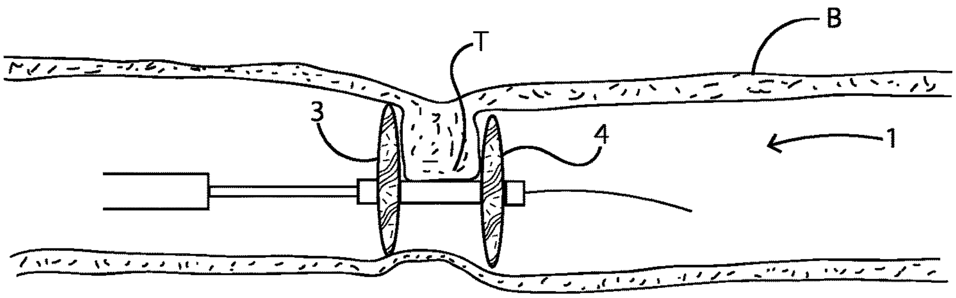

FIGS. 28(*a*), (*b*), and (*c*) show progression for movement of the probe 1 so that the bodies 3 and 4 are equally spaced on either side of a nodular polyp tumour T such as might be found in a pre-cancerous bowel B. As shown in FIG. 28(*c*) the longitudinal contraction of the bodies 3 and 4 can pinch the polyp tumour T and may have the effect of drawing it radially inwardly, thereby contributing to achievement of comprehensive treatment.

The colon, and even more so its inner mucosa can be readily manipulated by the moving baskets of the bolero thus drawing the target tissue in between the basket electrodes and thus bring the target tissue into the zone in which the strongest electric field will be delivered. The vessel wall is shown dipping in in FIG. 28(*c*) to help treat at the stalk of the lump which is key for full treatment.

The ability to pull tissue, both healthy and abnormal, into the area in which the electric field strength is highest will allow successful treatment of abnormal tissue and the margins around and beneath these abnormal tissues thus lowering the risk of recurrence which is largely a result of incomplete resection with current therapies where risk inherent in said therapies prevent physicians from treating. The ability to pull, grip or move tissue is primarily influenced by the electrode material, size and shape. The electrodes wires or struts must be sufficiently stiff if made from mesh or laser cut material to allow the electrode to move tissue without simply conforming to the tissue in situations where the tissue is pliable.

The following descriptions are examples of how this is achieved with a two-electrode design, these methods can be used for greater than two electrodes but may need to be altered somewhat. By each electrode having a maximum diameter in excess of the resting diameter of the lumen by a percentage in the range of 20% to 800% and preferably in the range of 20% to 500% means that during expansion the outermost edge of the basket will begin to interact with lumen tissue before the device has been fully expanded, continued actuation moves this outer most diameter outwards but also forwards towards the centre between the two electrodes thus somewhat gripping the tissue.

The electrode's ability to grip the tissue can be improved through the addition of lumps, tines or barbs to the electrode struts or wire thus improving the grip in a local area. In the case of a heat set Nitinol frame or mesh its geometric shape can be chosen such that the electrode achieves the diameter at which it contacts the vessel either closer to the spacer (for example the spacer 1803 in FIG. 22) between the electrodes or further away from this dependent on the intended tissue gripping strategy. This modifies the path in space through which individual elements of the electrode move. For example, the electrode shape identified as 2100, if used in a two-electrode device, would have the largest diameters of its body nearest to the electrode spacer 1803. As a product of its heat set shape there is a sharp change in wire mesh strand direction immediately beside the spacer 1803. This results in there being large, localised strain in this bend region when it is held down or constrained before actuation thus when the electrode is allowed to move via the actuator back towards its predetermined heat set shape this will result in immediate hinging of this face of the electrode towards the tissue, with this occurring on both sides of the target tissue the result is akin to a gripping action.

In addition, the ability to move the electrode bodies closer together during or after electrode expansion allows for the device to achieve a stronger tissue grip and potentially more consistent inter electrode distance than would otherwise be achievable. The ability to move the electrodes towards each other requires that the device be constructed such that the actuating members have sufficient tensile strength to create and maintain a grip on the tissue.

It is preferred that the electrodes can expand from about 1-2 mm pre-deployment to about 60 mm, and preferably to a maximum diameter in the range of 30 mm to 60 mm for the colon. This makes it particularly suitable for pulling tissue such as pre-cancerous nodules in the wall of the bowel, for example, but also in lumens such as anywhere in the GI tract oesophagus.

However, in other examples such as treatment of the bile duct the maximum diameter is preferably in the range of 4 mm to 10 mm, or 10 mm to 15 m for the urethra.

Figure 29A:
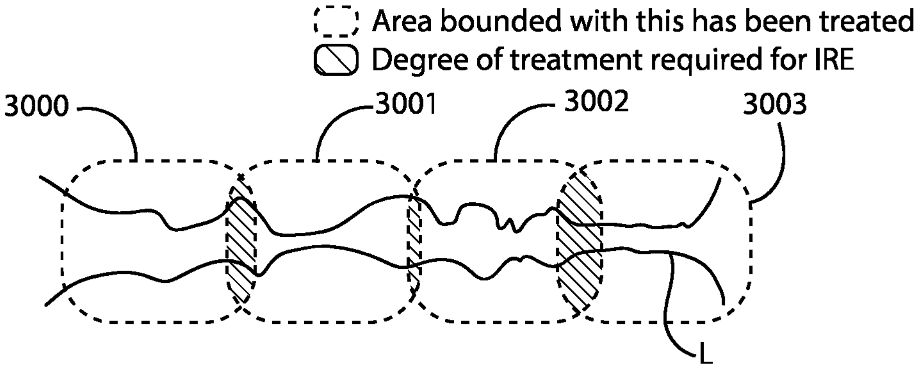
FIGS. 29(*a*) and 29(*b*) are a pair of diagrams showing (a) small areas with full irreversible electroporation (IRE) treatment, and (b) fully overlapping IRE areas for continuous IRE treatment along a length of a lumen.
Figure 29B:
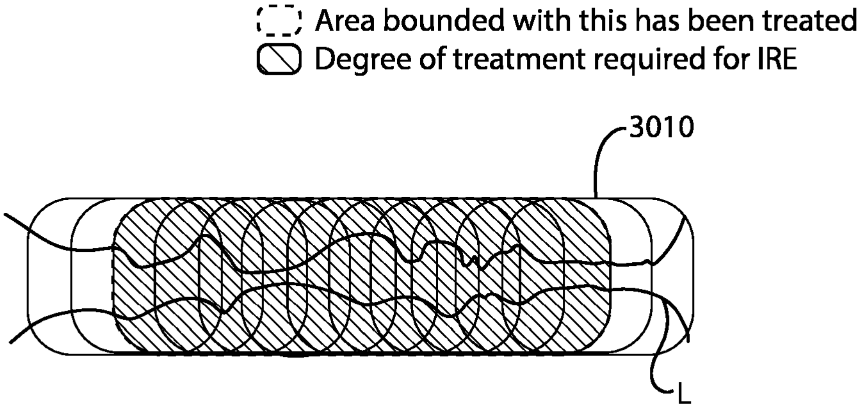

As shown in FIG. 29(*a*), where the tissue to be treated is longer than the spacing between the expanding bodies, the surgeon may move the probe 1 in increments providing treatment envelopes 3001, 3002, and 3003. However, the field which is generated may not be sufficient to achieve IRE, and so as shown in FIG. 29(*b*) these increments may be made short so that all space in the longitudinal direction has overlapped treatment. The surgeon may for example choose to have no overlap where RE is required, but full overlap where IRE is required.

The physician may in many cases, be in an environment where the GI tract is obstructed and thus the endoscope camera will have a somewhat obstructed view. With the "overlap technique" of FIGS. 29 (*a*) and (*b*) the physician can have less concern with each placement of the device on whether it is in the exact position they intended. This means the physician will be more comfortable using the device helping device uptake. When the probe is placed in vessels with highly variable geometry, as a result of the presence of cancer, strictures or patient anatomy, the electric field shape which is expected from the device will vary. Using an overlap technique will mean that the importance of each specific placement decreases as the device is repeatedly placed and re-placed. Correct choice of delivery dose will result in patients receiving one long "averaged" electric field that produces IRE in the required areas eliminating "cold" spots caused by small irregularities in device placement or contact.

Injection of a Fluid

The elongate support in various embodiments includes the guide wire and/or a shaft and an electrical conductor for conducting power to the electrodes. The electrodes may be individually driven via separate elongate conductors or driven together. The elongate support may also include one or more lumens as conduits for flow of a fluid to assist electroporation. The electroporation device may include a supply of fluid, such as a solution, or foam (gas and liquid). The fluid may be chosen for optimization of electrical characteristics and/or pharmaceutical or biological therapy. The fluid may be of any of the types described in our published patent specification WO2021/043779 the contents of which are incorporated herein by reference.

The fluid may be injected, or sprayed from, radial apertures in a shaft at or adjacent to the electrodes and/or via hollow needles which penetrate tissue in use. Such needles may have apertures along their length in addition to at their ends. The needles are connected to the proximal end/handle by means of an elongate member through which the solution is delivered.

The fluid may be in the form of a foam, being a liquid with very small bubbles of a gas. A foam may be used to enhance the permeabilization effect of electroporation, with particularly beneficial results for high frequency electroporation (greater than 100 KHz). Use of a foam is described in more detail below. In this specification the relative concentrations of liquid and gas in the foam are expressed by volume at atmospheric pressure, such as in a syringe when loaded with air and liquid.

The foam may be formed by any suitable means, and indeed it may be done manually by the clinician in a syringe.

A major benefit of utilising a foam for direct injection into the target tissue to be electroporated is that it can act as a carrier if required for the molecule of choice while its impact on tissue conductivity relative to a liquid is superior in that it minimises increases in the conductivity. The air or gas component of the foam bubbles have minimal conductivity relative to a liquid and enable a more favourable environment particularly in the case of high frequency (>100 kHz) pulses, minimising the current delivered and aiding in enhanced cell permeabilization.

The use of high frequency (>100 kHz) bipolar electrical pulses are advantageous for direct cell ablation or cell permeabilization for passive diffusion of molecules. The combination with a foam in some examples confers a benefit to the efficacy of the procedure (relative to using an equivalent liquid solution).

Non-foamed liquid when injected is rapidly diluted by the circulating blood volume. The interaction with blood decreases the efficacy of the liquid solution, due to binding with plasma proteins that ultimately reduces the number of active molecules. A foam on the other hand, is able to displace blood rather than mixing with it, increasing the contact time of a higher concentration of active agent with the tissue and thus resulting in greater efficacy. With foam, a lower concentration of agent can be used to obtain the same therapeutic effect as in their liquid counterpart, reducing the prevalence of side effects associated with higher concentrations.

A foam, due to the presence of bubbles of a gas such as air, is less conductive than the corresponding liquid solution and consequently results in lower currents, higher cell permeabilization and less pain sensation for the patient.

The presence of a cationic molecule within the solution or foam can reduce the electrical field strength required to electro permeabilise the cell wall. Examples of such cationic molecules include Lidocaine HCL.

Foam may in some examples be created by mixing albumin, gas, and a liquid solution, for example in a ratio of 1:4:1 by volume. Preferably, the ratio of gas (room air or CO2 gas for example) to liquid is in a range of 1:2 to 1:10 by volume.

Preferably, the foam used includes one or more of the following:

A foam being made largely of gas or air is less conductive than the corresponding liquid solution and consequently results in lower currents, higher cell permeabilization and less pain sensation for the patient.

Use of a foam injected into the environment to be electroporated will beneficially facilitate the treatment and the degree of cell permeabilization by not increasing the conductivity to the degree that a comparable liquid solution would. The following table sets out some preferred parameter ranges where a foam is injected, but these ranges advantageously apply to liquid injection.

| Treatment | Pulse Voltage V/cm | Pulse duration | Frequency Hz | Number of Pulses | Charge Delivered | Pulse Type |
|---|---|---|---|---|---|---|
| Electro-chemotherapy (ECT) | 500-1500 | 50-100 μsec | 1-5000 | 4-8 | N/A | Monopolar or Bipolar Square wave |
| Irreversible electroporation (IRE) | 1500-3000 | 70-100 μsec | 0.5-10 | 90-200 | N/A | Monopolar Square wave |
| High Freq Irreversible electroporation (HFIRE) | 2500-5000 | 1-5 μs | 100-500 KHz | >100 | N/A | Monopolar or Bipolar Square wave |
| Electroporation and Electrolysis (E2) | 100-3000 | μsec-milliseconds | N/A | N/A | >100 μF | Expo-nentially decaying wave |
| DNA/RNA delivery | 1-1000 | μsec-milliseconds | N/A | N/A | N/A | Monopolar Square wave |

Albumin, human serum albumin; concentration 10-50% preferably 15-30% by volume Polidocanol (0.5-5% by volume) or Sodium Tetradecyl Sulfate (STS) (0.5-5% by volume).

STS and Polidocanol are sclerosing agents individually, whereas Albumin is not Polidocanol is also a local anaesthetic.

Albumin is a foaming agent solely whereas Polidocanol and STS are both foaming and sclerosing agents (they are an irritant and induce cell death directly).

Active agents (the molecules being introduced) in solution may include one or more of:

Calcium ions, Ca++ (2 mMol to 150 mMol); Potassium (2 mMol to 100 mMol); lidocaine; lidocaine HCL; Bleomycin; Cisplatin; DNA; and/or RNA.

Preferably, the electroporation pulses advantageously have parameters as follows:

bipolar pulses 0.05 μs to 5 μs pulse lengths delivered in trains with an 'on' energised time per train of 0.1 μs to 1000 μs repeated up to 1000 times at a frequency of 1 kHz to 1000 KHz.

Injecting a foam directly into the environment surrounding the cells rather than a liquid-only substance with the same active agent results in a less conductive environment, enabling more efficient cell permeabilization aiding in the efficacy of electroporation-based treatments.

The efficacy of cell permeabilization (pores being created on the cell membrane) created by short bipolar electrical pulses (<50 μs) is impacted by the tissue conductivity. Higher conductivity of the liquid solution surrounding the cells will result in higher currents which is deleterious to the treatment resulting in poorer cell permeabilization and pain sensation in the patient.

Conductivity increases around the cell are caused in part by the volume of fluid in the area and the local injection of an electroporation solution, which may include a treatment molecule of choice (Calcium, Potassium, Bleomycin, Cisplatin, lidocaine HCL etc) and a large concentration of ions.

Utilising a foaming agent to deliver the therapeutic agent reduces the effect of a high conductivity on the efficacy of electroporation pulses to permeabilise cells.

A foam may also be utilised to facilitate dispersion of a local anaesthetic into the tissue to be treated. The local anaesthetic may be lidocaine 5-20 mg/ml with or without adrenaline. Mepivacaine 10 to 30 mg/ml is another example of a local anaesthetic that could be used. Lidocaine HCL presents as a cationic form of lidocaine and can reduce the electrical field strength required for electropermeabilisation of the cell wall. The foam and local anaesthetic could be administrated in combination with a molecule of choice e.g. calcium or potassium ions, bleomycin, DNA; or it could be provided alone.

Advantages

In one advantageous example the electrodes anchored to each other at the closest point with the opposing ends attached to two individual elongate members to facilitate compression which would impart a diameter increase in the electrodes and forcing them closer together to pinch the tissue. The electrodes may alternatively be self-expanding by shape memory material.

In one preferred example each electrode comprises a braided mesh of Nitinol or steel wire of diameter between 0.025 mm and 0.25 mm in a quantity of 8 to 96 wires and being arranged to collapse to sufficient size to fit through the biopsy channel (or other lumen) of an endoscope. The mesh engages with and stretches the tissue and forms a close-knit layer to ensure minimal apertures between the wires thereby providing a homogenous electrical field.

The mesh may have two separate layers, a structural layer of 0.15 mm to 0.35 mm wires in a quantity of 8 to 24 and a fine mesh layer of 0.01 mm to 0.1 mm wires in a quantity of 24 to 96, provide for an electrode which can collapse to sufficient size to fit through the biopsy channel (or other lumen) of an endoscope and where the structural layer would engage and stretch the tissue and the fines mesh layer would form a close knit layer to ensure minimal apertures between the wires thereby providing a homogenous electrical field.

It is preferred in some examples that there is heat setting of the electrodes such that they are predisposed to 'grow' parallel to the opposing electrode to achieve a consistent electrical field.

The actuator provides in some preferred examples an initial radial expansion to return to its predefined diameter. Further actuation of the handle promotes dilation of soft/compliant tissue, or, conforming to the shape of hard/stenosed tissue. The initial expansion may be to a diameter of 20 mm to 40 mm. It is easy to open the electrodes up "in free space" with the handle but is difficult to push them into tissue aggressively. Each electrode "wants" to expand and foreshorten and since it is so easy to open the mesh before it contacts tissue, once it contacts tissue it is immediately clear to the user as the force required to actuate increases drastically. This acts as a very evident safety feature.

The electrode outer diameter is designed to be larger than the relaxed diameter of the target anatomy but never to exceed the maximum dilated diameter of the anatomy to avoid damage/tearing. For example, for the colon this range is minimum of 10 mm and maximum of 40 to 60 mm. This also ensures adequate wall contact of the electrode.

In some advantageous examples, the actuation caused by the user is coupled to both electrodes in such a way that if one is constrained the other continues expanding—this ensures both electrodes open until they engage tissue and then provide a balanced pressure on the tissue at each electrode. The way we achieved this on current design is through the spacer/insulator 5 being attached to each electrode at its ends but otherwise free to move along the central shaft of the device.

It will be appreciated that the invention achieves optimal electroporation whilst avoiding the risk of dissection or perforation. The delivery system is capable of being delivered at a low profile, ideally through the biopsy channel of the endoscope, furthermore (a) for healthy tissue, the electrode embeds into the soft tissue and (b) for diseased tissue which is stenosed or having reduced elasticity, the electrode conforms to the surface of the treated tissue with a force that does not cause undue distention of the tissue resulting in tissue damage. Additionally, the tissue may be a mix of elastic and non-elastic tissue where the device must automatically accommodate both tissue types.

The probe of the invention provides low profile, catheter access to a narrowed or restricted lumen such as in the gastrointestinal tract.

There may be Bipolar electrode drive adjustable according to position between the collapsed and expanded (operative) states.

Treatment can be very effectively applied around a full circumference of a lumen or tissue.

The probe allows delivery of uniform, circumferential EP (electroporation) energy to a tumor. This is enhanced if the electrodes are flexible, on the surface of a flexible balloon, or due to flexibility of an expanding mesh or basket with sufficient stiffness to maintain electrode-tissue contact but not sufficient to cut into the tissue.

The probe allows delivery of EP energy to sufficient tumor volume and depth whilst minimizing risk of tissue dissection/lumen perforation. This is achieved particularly well where the probe includes tines or barbs, and/or where the electrode bodies are configured to pinch the tissue.

The probe may provide haptic feedback to assist optimal contact between the electrodes and patient tissue. Another optional advantageous feature is delivery of a fluid such as foam to the site to modulate conductivity.

Ability to Deliver High Voltage to Tissue Whilst Reducing Current

Treatment can be applied around 360° (or variations in-between e.g. 180° electrical coverage, with 180° insulated/non-conductive elements to allow for circumstances where a full circumferential treatment is not required or desired), and there is excellent versatility due to the fact that any desired subset of the electrodes may be driven according to either user control inputs, or automatic feedback from sensors detecting parameters such as pressure of an electrode against tissue, degree of expansion or radial position of an electrode.

The devices allow tissue to fall between the arms/struts to maximise the volume of tissue treated.

Devices of the invention may be used for reversible electroporation for electroporation in combination with chemotherapy, Electrochemotherapy (ECT), or with calcium. It has the additional advantage that tumour tissues take up more of the active substance than healthy cells due to their increased conductivity and thus healthy cells can be within the treatment area without this causing excess additional risk to the patient.

Irreversible cell membrane permeabilisation may potentially be achieved at a reduced electrical field strength through the presence of a cationic solution.

The device allows for generation of a variety of electrical fields and can extend the depth of treatment into tissue depending on the specific tumour being treated. The invention is not limited to the embodiments described but may be varied in construction and detail.

The invention claimed is:

1. An electroporation probe comprising:

an elongate support, the support comprising electrical conductors and being configured to extend through a lumen of a human or animal body extending in a longitudinal direction with a longitudinal axis from a proximal end to a distal end, at least two electroporation electrodes supported by the support and being connected to the conductors and being mounted to engage tissue in the wall of a lumen in use, a spacer between axially juxtaposed electrodes, and an electrode mechanical actuator, wherein the at least two electroporation electrodes are deformable for radial expansion from a retracted position, said spacer comprises a plurality of parallel spacer elements maintaining separation of the at least two electroporation electrodes even at furthest portions of the at least two electroporation electrodes from the longitudinal axis when the at least two electroporation electrodes are radially expanded.

2. The electroporation probe as claimed in claim 1, wherein said radial expansion causes surfaces of a pair of electrodes to move closer together in the longitudinal direction with radial expansion, thereby contributing to gripping of tissue which protrudes internally into a lumen.

3. The electroporation probe as claimed in claim 1, wherein the proximal end of a proximal electrode and the distal end of a distal electrode are each coupled to the actuator to cause said ends to move toward each other to compress the electrodes against the spacer.

4. The electroporation probe as claimed in claim 1, wherein at least one of the electrodes has a shape memory and is configured for at least some of said radial expansion upon removal of a constraint.

5. The electroporation probe as claimed in claim 1, wherein the actuator is configured to cause axial compression of at least one electrode to force at least some of said radial expansion; and wherein the electrode has a preferred expanded shape memory state to guide initial radial expansion and the actuator is configured to cause further radial expansion, and the actuator is configured to allow a user to sense a level of force required by the actuator to cause radial expansion, thereby providing a user indication of when tissue is engaged and to what extent the tissue is being pushed by said further radial expansion.

6. The electroporation probe as claimed in claim 1, wherein at least one electrode is configured for radial expansion to exert a radial force to dilate soft, compliant tissue yet conform to harder stenosed tissue without causing dissection or perforation, said force being in the range of 0.1 $N/mm^2$ to 1 $N/mm^2$.

7. The electroporation probe as claimed in claim 1, wherein at least one electrode comprises a mesh comprising a structural layer of 8 to 24 wires having a diameter in the range of 0.15 mm to 0.35 mm, and a fine layer of 24 to 96 wires of diameter in the range of 0.01 mm to 0.1 mm.

8. The electroporation probe as claimed in claim 1, wherein the length in the longitudinal direction of at least one electrode is in the range of 0.5 mm to 75 mm; and wherein the longitudinal distance between at least two electrodes is in the range of 2 mm to 20 mm.

9. The electroporation probe as claimed in claim 1, wherein the probe comprises at least two electrodes of different stiffness, configured for different levels of penetration into tissue.

10. The electroporation probe as claimed in claim 1, wherein the deformable body comprises an expandable mesh.

11. The electroporation probe as claimed in claim 1, wherein at least one electrode comprises a feature for extending radially into tissue in use.

12. The electroporation probe as claimed in claim 1, further comprising a physical separator between axially juxtaposed electrodes.

13. The electroporation probe as claimed in claim 1, further comprising a physical separator between axially juxtaposed electrodes; and wherein the probe comprises proximal and distal barrier balloons defining a space, in use, enclosing at least two expanding bodies, the space being to enclose a fluid agent introduced into the space to assist electroporation.

14. An electroporation device comprising a probe of claim 1 and an electrical drive for delivering pulses to the electrodes via the elongate support conductor.

15. The device as claimed in claim 14, wherein the electrical drive is configured to independently apply variable voltages, wherein the electrical drive is configured to provide pulses matching, or specific to, the electrode position; and wherein the actuator is configured to move the electrodes to an intermediate position between said retracted and operative positions, and the electrical drive is configured to provide pulses matching the intermediate electrode position.

16. The device as claimed in claim 14, wherein the drive allows selective activation of specific electrodes.

17. The device as claimed in claim 14, comprising an endoscope and wherein the probe has lateral dimensions in the retracted position to allow entry to the body via an endoscope instrument channel; and wherein at least some electrodes are movable axially, and the actuator is configured to move at least one electrode to optimise electrode spacing.

18. The device as claimed in claim 14, wherein the probe comprises a conduit extending distally for delivery of a fluid at or near the electrodes; and wherein the electrical drive is configured to control drive pulses according to delivery of a fluid.

19. A method of use of a device of claim 14, the method comprising inserting the probe along a lumen of a human or animal body until the electrodes are located at a longitudinal position of tissue to be treated, and actuating the electrodes to perform electroporation treatment of the tissue.

20. The electroporation probe as claimed in claim 1, wherein the probe is for treatment of the GI tract and a maximum diameter after radial expansion is in the range of 30 to 60 mm.

21. The electroporation probe as claimed in claim 1, wherein at least one electrode comprises a feature for extending radially into tissue in use, and the feature comprises a barb or a needle, and a laser cut tube has a barb feature as part of its laser cut pattern.

22. The electroporation probe as claimed in claim 1, wherein the probe comprises a catheter and there are eight parallel spacer members between two electrodes and said spacer members are equally circumferentially spaced apart around the longitudinal axis.

* * * * *